US010517728B2

(12) United States Patent
Vidlund et al.

(10) Patent No.: US 10,517,728 B2
(45) Date of Patent: Dec. 31, 2019

(54) DEVICES AND METHODS FOR POSITIONING AND MONITORING TETHER LOAD FOR PROSTHETIC MITRAL VALVE

(71) Applicant: Tendyne Holdings, Inc., Roseville, MN (US)

(72) Inventors: Robert M. Vidlund, Forest Lake, MN (US); Craig A. Ekvall, East Bethel, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 370 days.

(21) Appl. No.: 15/251,269

(22) Filed: Aug. 30, 2016

(65) Prior Publication Data

US 2016/0367368 A1 Dec. 22, 2016

Related U.S. Application Data

(63) Continuation of application No. PCT/US2015/019418, filed on Mar. 9, 2015.
(Continued)

(51) Int. Cl.
*A61F 2/24* (2006.01)
*A61B 90/00* (2016.01)

(52) U.S. Cl.
CPC .......... *A61F 2/2487* (2013.01); *A61B 90/06* (2016.02); *A61F 2/2466* (2013.01);
(Continued)

(58) Field of Classification Search
CPC .... A61F 2/2427; A61F 2/2457; A61F 2/2466; A61F 2/248; A61F 2/2487; A61F 2/95;
(Continued)

(56) References Cited

U.S. PATENT DOCUMENTS 2,697,008 A 12/1954 Rowley
3,409,013 A 11/1968 Berry
(Continued)

FOREIGN PATENT DOCUMENTS

CN 1486161 3/2004
CN 1961845 A 5/2007
(Continued)

OTHER PUBLICATIONS

US 9,155,620 B2, 10/2015, Gross et al. (withdrawn)
(Continued)

*Primary Examiner* — Robert A Lynch
(74) *Attorney, Agent, or Firm* — Lerner, David, Littenberg, Krumholz & Mentlik, LLP

(57) ABSTRACT

Apparatus and methods are described herein for positioning an epicardial anchor device and measuring the load of a tether extending from a prosthetic heart valve and coupled to the epicardial anchor device. In some embodiments, an apparatus includes a handle assembly coupled to an elongate member and a docking member coupled to a distal end of the elongate member. The docking member can be releasably coupled to an epicardial anchor device configured to secure a tether extending from a prosthetic heart valve implanted with a heart at a location on an exterior of a ventricular wall of the heart. A force sensor device is coupled to the handle assembly and can measure a force exerted on the force sensor device. The force is associated with a tension of the tether extending through the elongate member and handle assembly.

20 Claims, 33 Drawing Sheets

Related U.S. Application Data

(60) Provisional application No. 61/950,429, filed on Mar. 10, 2014, provisional application No. 61/970,887, filed on Mar. 26, 2014, provisional application No. 61/970,882, filed on Mar. 26, 2014.

(52) U.S. Cl.
CPC ....... *A61B 2090/064* (2016.02); *A61F 2/2418* (2013.01); *A61F 2/2427* (2013.01); *A61F 2/2457* (2013.01)

(58) Field of Classification Search
CPC ...... A61F 2002/2484; A61F 2002/9517; A61F 2220/0008; A61B 17/0401; A61B 2017/0409; A61B 2090/064
See application file for complete search history.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Sammuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane et al. |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro et al. |
| 6,077,214 A | 6/2000 | Mortier et al. |

(56) References Cited

U.S. PATENT DOCUMENTS

| | | |
|---|---|---|
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely et al. |
| 6,575,252 B2 | 6/2003 | Reed |
| 6,582,462 B1 | 6/2003 | Andersen et al. |
| 6,605,112 B1 | 8/2003 | Moll |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |

(56) References Cited

U.S. PATENT DOCUMENTS

| | | | |
|---|---|---|---|
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Thambar et al. |
| 8,986,376 B2 | 3/2015 | Solem |
| 9,011,522 B2 | 4/2015 | Annest et al. |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Sequin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 2001/0018611 A1 | 8/2001 | Solem et al. |
| 2001/0021872 A1 | 9/2001 | Bailey et al. |
| 2001/0025171 A1* | 9/2001 | Mortier ............ A61B 17/00234 606/1 |
| 2001/0032517 A1* | 10/2001 | Reinemann, Jr. ...... G01L 5/0033 73/826 |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | Van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino |
| 2005/0203614 A1 | 9/2005 | Forster et al. |

(56) References Cited

U.S. PATENT DOCUMENTS

| | | |
|---|---|---|
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Randert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariiler |
| 2007/0270932 A1 | 11/2007 | Headley et al. |
| 2007/0270943 A1 | 11/2007 | Solem |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |

(56) References Cited

U.S. PATENT DOCUMENTS

| | | |
|---|---|---|
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2010/0305576 A1* | 12/2010 | Ferguson ............ A61B 17/0401 606/104 |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund et al. |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James et al. |
| 2015/0202044 A1 | 7/2015 | Chau et al. |
| 2015/0216653 A1 | 8/2015 | Freudenthanl |
| 2015/0216660 A1 | 8/2015 | Pintor et al. |
| 2015/0223820 A1 | 8/2015 | Olson et al. |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan et al. |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss et al. |
| 2016/0262879 A1 | 9/2016 | Meiri et al. |
| 2016/0262881 A1 | 9/2016 | Schankereli et al. |

(56) References Cited

U.S. PATENT DOCUMENTS

| | | |
|---|---|---|
| 2016/0278955 A1 | 9/2016 | Liu et al. |
| 2016/0317290 A1 | 11/2016 | Chau et al. |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |
| 2018/0263618 A1 | 9/2018 | Vidlund et al. |

FOREIGN PATENT DOCUMENTS

| | | |
|---|---|---|
| CN | 2902226 | 5/2007 |
| CN | 101146484 | 3/2008 |
| CN | 101180010 | 5/2008 |
| CN | 101984938 | 3/2011 |
| CN | 102869317 | 1/2013 |
| CN | 102869318 | 1/2013 |
| CN | 102869321 | 1/2013 |
| CN | 103220993 | 7/2013 |
| CN | 102639179 B | 10/2014 |
| DE | 2246526 | 3/1973 |
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049815 | 4/2002 |
| DE | 102006052564 | 12/2007 |
| DE | 102006052710 | 5/2008 |
| DE | 102007043830 A1 | 4/2009 |
| DE | 102007043831 | 4/2009 |
| EP | 0103546 | 5/1988 |
| EP | 1057460 | 12/2000 |
| EP | 1088529 | 4/2001 |
| EP | 1469797 | 11/2005 |
| EP | 2111800 | 10/2009 |
| EP | 2111800 A1 | 10/2009 |
| EP | 2193762 | 6/2010 |
| EP | 2747707 | 4/2015 |
| EP | 2918248 | 9/2015 |
| EP | 2278944 | 3/2016 |
| FR | 2788217 | 7/2000 |
| FR | 2815844 | 5/2002 |
| JP | 2003-505146 | 2/2003 |
| JP | 2004045217 A | 2/2004 |
| JP | 2005-515836 | 6/2005 |
| JP | 2009-514628 | 4/2009 |
| JP | 2009-519783 | 5/2009 |
| JP | 2013-512765 | 4/2013 |
| NL | 1017275 | 8/2002 |
| SU | 1271508 | 11/1986 |
| WO | WO 92/17118 | 10/1992 |
| WO | WO 93/01768 | 2/1993 |
| WO | WO 98/29057 | 7/1998 |
| WO | WO 99/40964 | 8/1999 |
| WO | WO 99/47075 | 9/1999 |
| WO | WO 2000/018333 | 4/2000 |
| WO | WO 2000/030550 | 6/2000 |
| WO | WO 2000/041652 | 7/2000 |
| WO | WO 2000/047139 | 8/2000 |
| WO | WO 2001/035878 | 5/2001 |
| WO | WO 2001/049213 | 7/2001 |
| WO | WO 2001/054624 | 8/2001 |
| WO | WO 2001/054625 | 8/2001 |
| WO | WO 2001/056512 | 8/2001 |
| WO | WO 2001/061289 | 8/2001 |
| WO | WO 2001/076510 | 10/2001 |
| WO | WO 2001/082840 | 11/2001 |
| WO | WO 2002/004757 | 1/2002 |
| WO | WO 2002/022054 | 3/2002 |
| WO | WO 2002/028321 | 4/2002 |
| WO | WO 2002/036048 | 5/2002 |
| WO | WO 2002/041789 | 5/2002 |
| WO | WO 2002/043620 | 6/2002 |
| WO | WO 2002/049540 | 6/2002 |
| WO | WO 2002/076348 | 10/2002 |
| WO | WO 2003/003943 | 1/2003 |
| WO | WO 2003/030776 | 4/2003 |
| WO | WO 2003/047468 | 6/2003 |
| WO | WO 2003/049619 | 6/2003 |
| WO | WO 2004/019825 | 3/2004 |
| WO | WO 2005/102181 | 11/2005 |
| WO | WO 2006/014233 | 2/2006 |
| WO | WO 2006/034008 | 3/2006 |
| WO | WO 2006/064490 | 6/2006 |
| WO | WO 2006/070372 | 7/2006 |
| WO | WO 2006/105009 | 10/2006 |
| WO | WO 2006/113906 | 10/2006 |
| WO | WO 2006/127756 | 11/2006 |
| WO | WO 2007/081412 | 7/2007 |
| WO | WO 2007/100408 | 9/2007 |
| WO | WO 2008/005405 | 1/2008 |
| WO | WO 2008/035337 | 3/2008 |
| WO | WO 2008/091515 | 7/2008 |
| WO | WO 2008/125906 | 10/2008 |
| WO | WO 2008/147964 | 12/2008 |
| WO | WO 2009/024859 | 2/2009 |
| WO | WO 2009/026563 | 2/2009 |
| WO | WO 2009/045338 | 4/2009 |
| WO | WO 2009/132187 | 10/2009 |
| WO | WO 2010/090878 | 8/2010 |
| WO | WO 2010/098857 | 9/2010 |
| WO | WO 2010/121076 | 10/2010 |
| WO | WO 2011/017440 | 2/2011 |
| WO | WO 2011/022658 | 2/2011 |
| WO | WO 2011/069048 | 6/2011 |
| WO | WO 2011/072084 | 6/2011 |
| WO | WO 2011/106735 | 9/2011 |
| WO | WO 2011/109813 | 9/2011 |
| WO | WO 2011/159342 | 12/2011 |
| WO | WO 2011/163275 | 12/2011 |
| WO | WO 2012/027487 | 3/2012 |
| WO | WO 2012/036742 | 3/2012 |
| WO | WO 2012/095116 | 7/2012 |
| WO | WO 2012/177942 | 12/2012 |
| WO | 2013/028387 A2 | 2/2013 |
| WO | WO 2013/045262 | 4/2013 |
| WO | WO 2013/059747 | 4/2013 |
| WO | WO 2013/096411 | 6/2013 |
| WO | WO 2013/175468 | 11/2013 |
| WO | WO 2014/121280 | 8/2014 |
| WO | WO 2014/144937 | 9/2014 |
| WO | WO 2014/162306 | 10/2014 |
| WO | WO 2014/189974 | 11/2014 |
| WO | WO 2015/051430 | 4/2015 |
| WO | WO 2015/058039 | 4/2015 |
| WO | WO 2015/063580 | 5/2015 |
| WO | WO 2015/065646 | 5/2015 |
| WO | WO 2015/120122 | 8/2015 |
| WO | WO 2015/138306 | 9/2015 |
| WO | WO 2015/173609 | 11/2015 |
| WO | WO 2016/112085 | 7/2016 |
| WO | WO 2016/126942 | 8/2016 |
| WO | WO 2016/168609 | 10/2016 |
| WO | WO 2016/196933 | 12/2016 |
| WO | WO 2017/096157 | 6/2017 |
| WO | WO 2017/132008 | 8/2017 |

(56) References Cited

FOREIGN PATENT DOCUMENTS

| WO | WO 2017/218375 | 12/2017 |
|---|---|---|
| WO | WO 2018/005779 | 1/2018 |
| WO | WO 2018/013515 | 1/2018 |

OTHER PUBLICATIONS

Second Office Action for Chinese Application No. 201580011812.9, dated Apr. 9, 2018, 4 pages.

Al Zaibag, M. et al., "Percutaneous Balloon Valvotomy in Tricuspid Stenosis," British Heart Journal, Jan. 1987, 57(1):51-53.

Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.

Almagor, Y. et al., "Balloon Expandable Stent Implantation in Stenotic Right Heart Valved Conduits," Journal of the American College of Cardiology, Nov. 1, 1990, 16(6):1310-1314.

Andersen, H. R. et al., "Transluminal implantation of artificial heart valves. Description of a new expandable aortic valve and initial results with implantation by catheter technique in closed chest pigs," European Heart Journal, 1992, 13(5):704-708.

Andersen, H. R., "History of Percutaneous Aortic Valve Prosthesis," Herz, Aug. 2009, 34(5):343-346.

Andersen, H. R., "Transluminal catheter implanted prosthetic heart valves," International Journal of Angiology, 1998, 7(2):102-106.

Ashton, R. C., Jr. et al., "Development of an Intraluminal Device for the Treatment of Aortic Regurgitation: Prototype and in Vitro Testing System," Journal of Thoracic and Cardiovascular Surgery, 1996, 112:979-983.

Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.

Bernacca, G. M. et al., "Polyurethane heart valves: Fatigue failure, calcification, and polyurethane structure," Journal of Biomedical Materials Research, Mar. 5, 1997, 34(3):371-379.

Boudjemline, Y. et al., "Steps Toward the Percutaneous Replacement of Atrioventricular Valves: An Experimental Study," Journal of the American College of Cardiology, Jul. 2005, 46(2):360-365.

Buckberg, G. et al., "Restoring Papillary Muscle Dimensions During Restoration in Dilated Hearts," Interactive CardioVascular and Thoracic Surgery, 2005, 4:475-477.

Chamberlain, G., "Ceramics Replace Body Parts," Design News, Jun. 9, 1997, Issue 11, vol. 52, 5 pages.

Choo, S. J. et al., "Aortic Root Geometry: Pattern of Differences Between Leaflets and Sinuses of Valsava," The Journal of Heart Valve Disease, Jul. 1999, 8:407-415.

Declaration of Malcolm J. R. Dalrymple-Hay, Nov. 9, 2012, pp. 1-11; with Curriculum Vitae, Oct. 4, 2012.

Dotter, C. T. et al., "Transluminal Treatment of Arteriosclerotic Obstruction. Description of a New Technic and a Preliminary Report of its Application," Circulation, Nov. 1964, 30:654-670.

Drawbaugh, K., "Feature—Heart Surgeons Explore Minimally Invasive Methods," Reuters Limited, Jul. 16, 1996, 3 pages.

Gray, H., The Aorta, Anatomy of the Human Body, 1918, Retrieved from the Internet <http://www.bartleby.com/107/142.html>, Dec. 10, 2012, 5 pages.

Gray, H., The Heart, Anatomy of the Human Body, 1918, Retrieved from the Internet <http://education.yahoo.com/reference/gray/subjects/subject/138>, Aug. 10, 2012, 9 pages.

Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.

Inoue, K. et al., "Clinical Application of Transvenous Mitral Commissurotomy by a New Balloon Catheter," The Journal of Thoracic and Cardiovascular Surgery, 1984, 87:394-402.

Jin, X. Y. et al., "Aortic Root Geometry and Stentless Porcine Valve Competence," Seminars in Thoracic and Cardiovascular Surgery, Oct. 1999, 11(4):145-150.

Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.

Kolata, G., "Device That Opens Clogged Arteries Gets a Failing Grade in a New Study," New York Times [online], <http://www.nytimes.com/1991/01/03/health/device-that-opens-clogged-arteries-gets-a-faili . . . ,>, published Jan. 3, 1991, retrieved from the Internet on Feb. 5, 2016, 3 pages.

Lawrence, D. D., "Percutaneous Endovascular Graft: Experimental Evaluation," Radiology, 1987, 163:357-360.

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.

Lutter, G. et al., "Mitral Valved Stent Implantation," European Journal of Cardio-Thoracic Surgery, 2010, 38:350-355, 2 pages.

Ma, L. et al., "Double-crowned valved stents for off-pump mitral valve replacement," European Journal of Cardio-Thoracic Surgery, Aug. 2005, 28(2):194-198.

Moazami, N. et al., "Transluminal aortic valve placement: A feasibility study with a newly designed collapsible aortic valve," ASAIO Journal, Sep./ Oct. 1996, 42(5):M381-M385.

Orton, C., "Mitralseal: Hybrid Transcatheter Mitral Valve Replacement," Retrieved from the Internet: <http:/www.acvs.org/symposium/proceedings2011/data/papers/102.pdf>, pp. 311-312.

Pavcnik, D. et al. "Development and Initial Experimental Evaluation of a Prosthetic Aortic Valve for Transcatheter Placement," Radiology, 1992; 183:151-154.

Porstmann, W. et al., "Der Verschlug des Ductus Arteriosus Persistens ohne Thorakotomie," Thoraxchirurgie Vaskuläre Chirurgie, Band 15, Heft 2, Stuttgart, Apr. 1967, pp. 199-203.

Rashkind, W. J., "Creation of an Atrial Septal Defect Without Thoracotomy," The Journal of the American Medical Association, Jun. 13, 1966, 196(11):173-174.

Rashkind, W. J., "Historical Aspects of Interventional Cardiology: Past, Present, Future," Texas Heart Institute Journal, Dec. 1986, 13(4):363-367.

Reul, H. et al., "The Geometry of the Aortic Root in Health, at Valve Disease and After Valve Replacement," J. Biomechanics, 1990, 23(2):181-191.

Rosch, J. et al., "The Birth, Early Years and Future of Interventional Radiology," J Vasc Interv Radiol., Jul. 2003, 4:841-853.

Ross, D. N., "Aortic Valve Surgery," Guy's Hospital, London, 1968, pp. 192-197.

Rousseau, E. P. M. et al., "A mechanical analysis of the closed Hancock heart valve prosthesis," Journal of Biomechanics, 1988, 21(7):545-562.

Sabbah, A. N. et al., "Mechanical Factors in the Degeneration of Porcine Bioprosthetic Valves: An Overview," Dec. 1989, Journal of Cardiac Surgery, 4(4):302-309.

Selby, J. B., "Experience with New Retrieval Forceps for Foreign Body Removal in the Vascular, Urinary, and Biliary Systems," Radiology, 1990, 176:535-538.

Serruys, P. W. et al., "Stenting of Coronary Arteries. Are we the Sorcerer's Apprentice?," European Heart Journal , Sep. 1989, 10(9):774-782.

"Shape Memory Alloys," Retrieved from the Internet: <http://webdocs.cs.ualberta.ca/~database/MEMS/sma.html>, Feb. 5, 2016, 3 pages.

Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.

Tofeig, M. et al., "Transcatheter Closure of a Mid-Muscular Ventricular Septal Defect with an Amplatzer VSD Occluder Device," Heart, 1999, 81:438-440.

Uchida, B. T. et al., "Modifications of Gianturco Expandable Wire Stents," Am. J. Roentgenol., May 1988, 150(5):1185-1187.

(56) References Cited

OTHER PUBLICATIONS

Watt, A. H. et al., "Intravenous Adenosine in the Treatment of the Supraventricular Tachycardia; a Dose-Ranging Study and Interaction with Dipyridamole," British Journal of Clinical Pharmacology, 1986, 21:227-230.

Webb, J. G. et al., "Percutaneous Aortic Valve Implantation Retrograde from the Femoral Artery," Circulation, 2006, 113:842-850.

Wheatley, D. J., "Valve Prostheses," Rob & Smith's Operative Surgery, Fourth Edition, 1986, pp. 415-424, Butterworths.

Yoganathan, A. P. et al., "The Current Status of Prosthetic Heart Valves," In Polymetric Materials and Artificial Organs, American Chemical Society, 1984, pp. 111-150.

First Office Action for Chinese Application No. 201580011812.9, dated Aug. 30, 2017, 9 pages.

Office Action for European Application No. 15711384.6, dated Oct. 18, 2016, 2 pages.

International Search Report and Written Opinion for International Application No. PCT/US2015/019418, dated Sep. 10, 2015, 16 pages.

\* cited by examiner

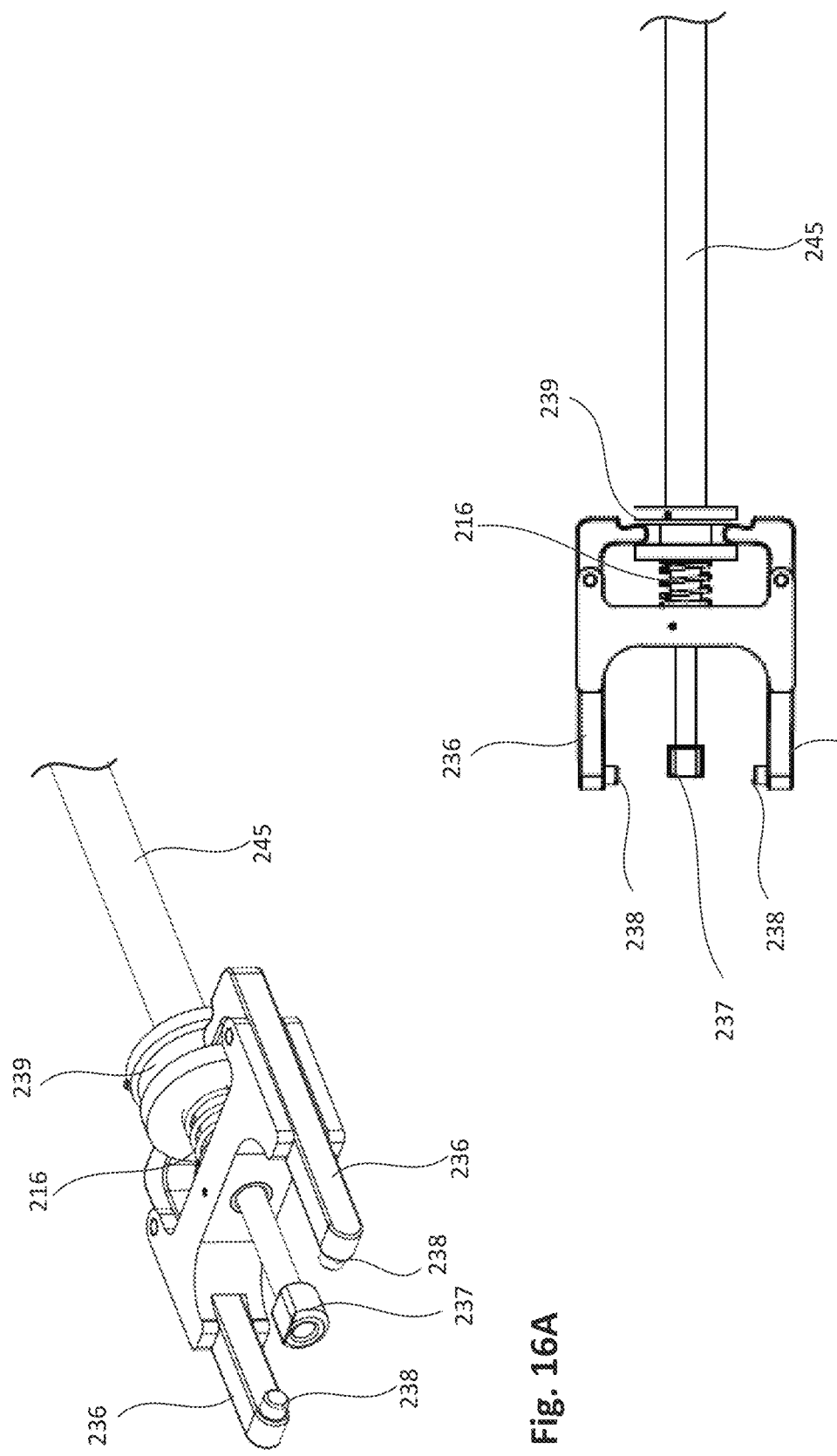

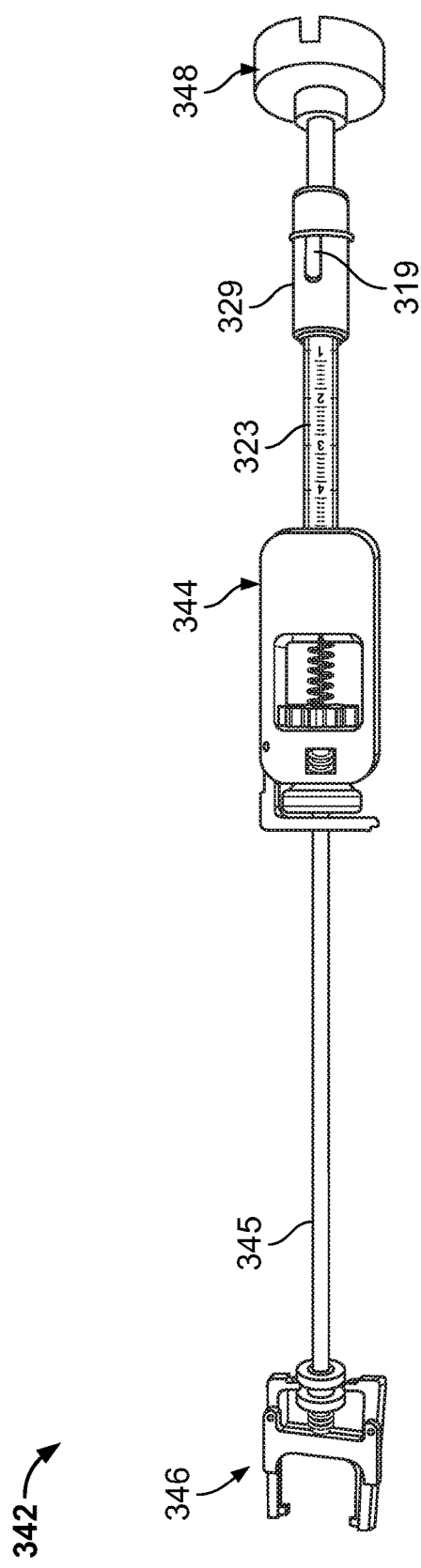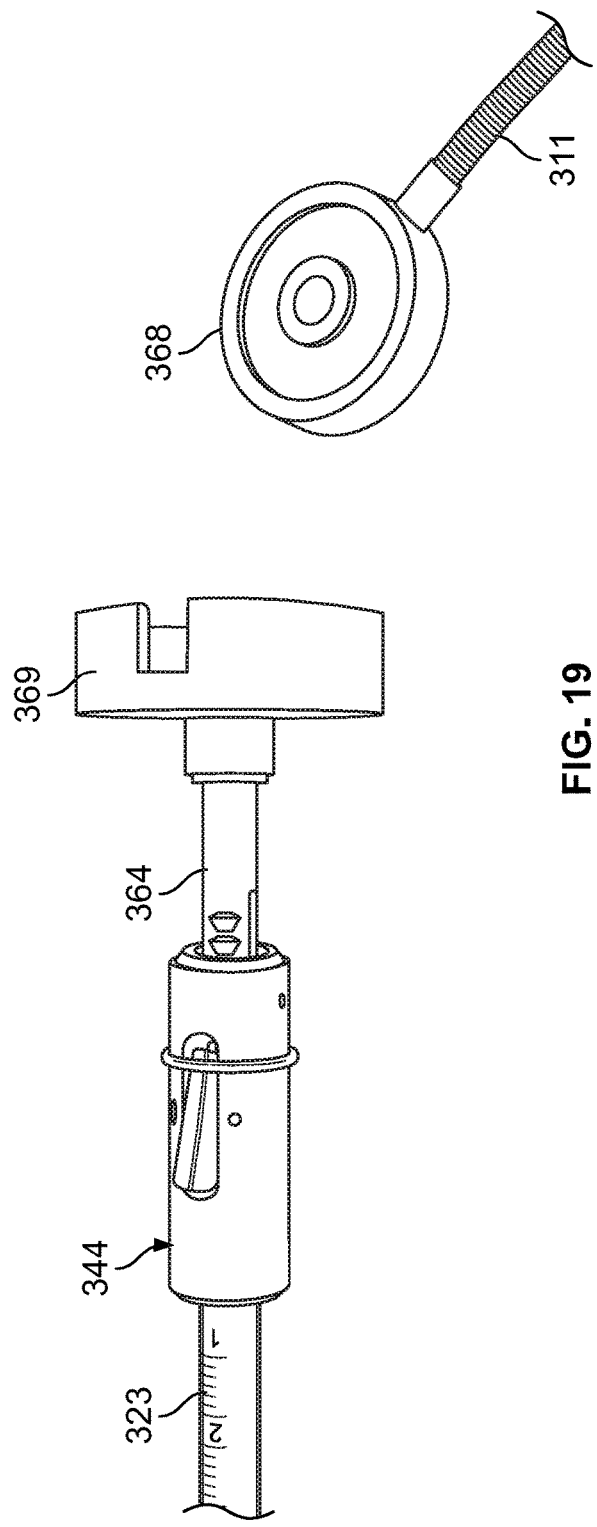
FIG. 18
FIG. 19

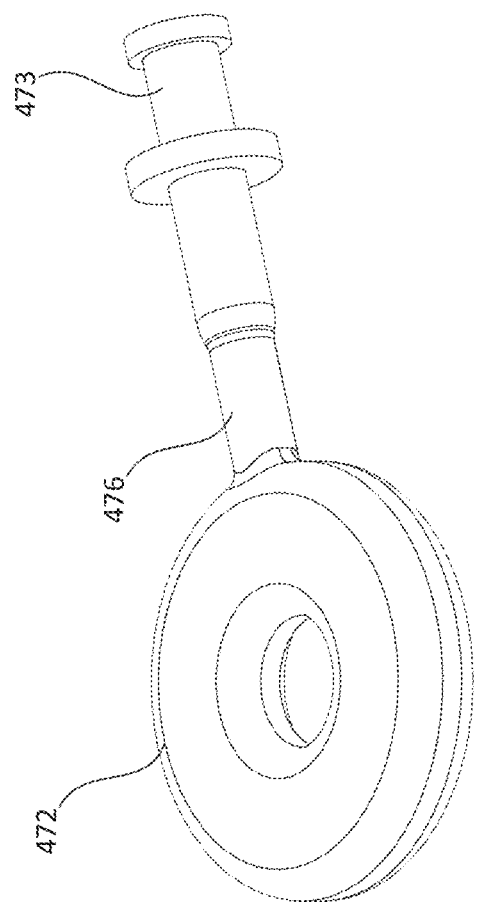

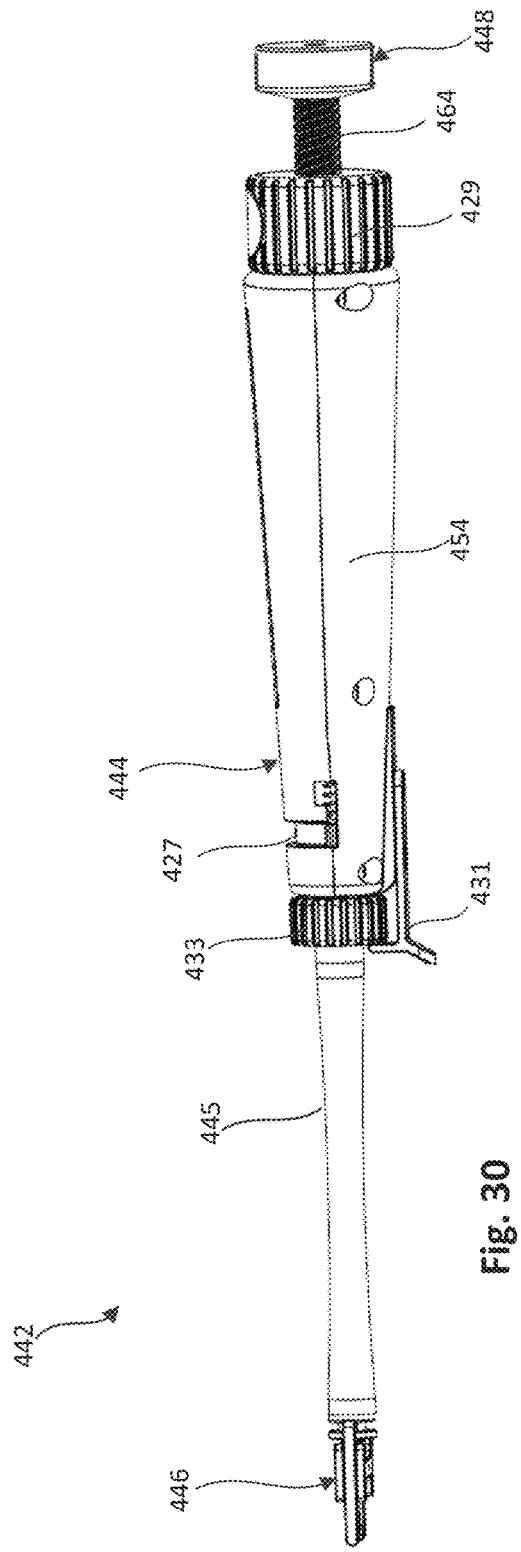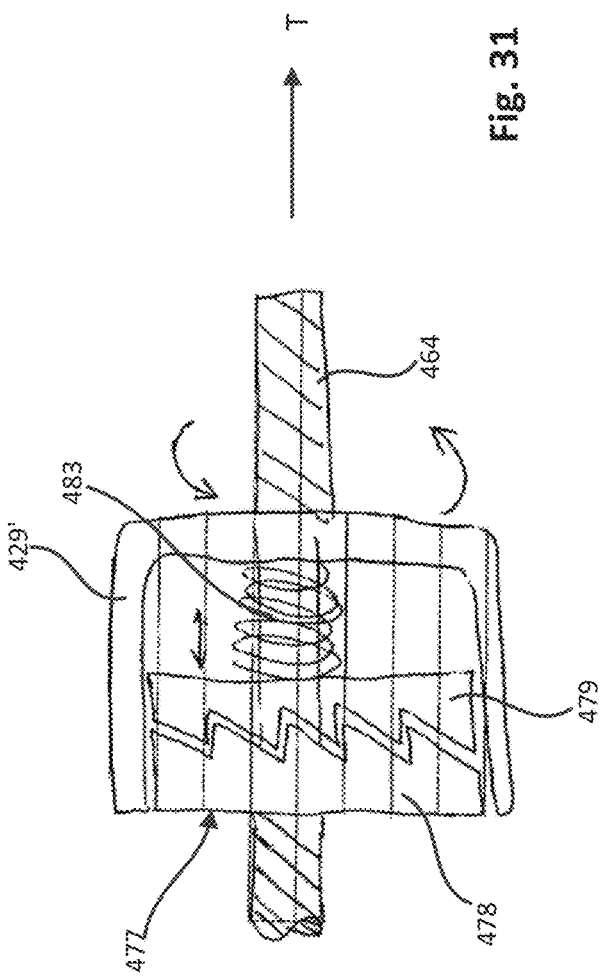

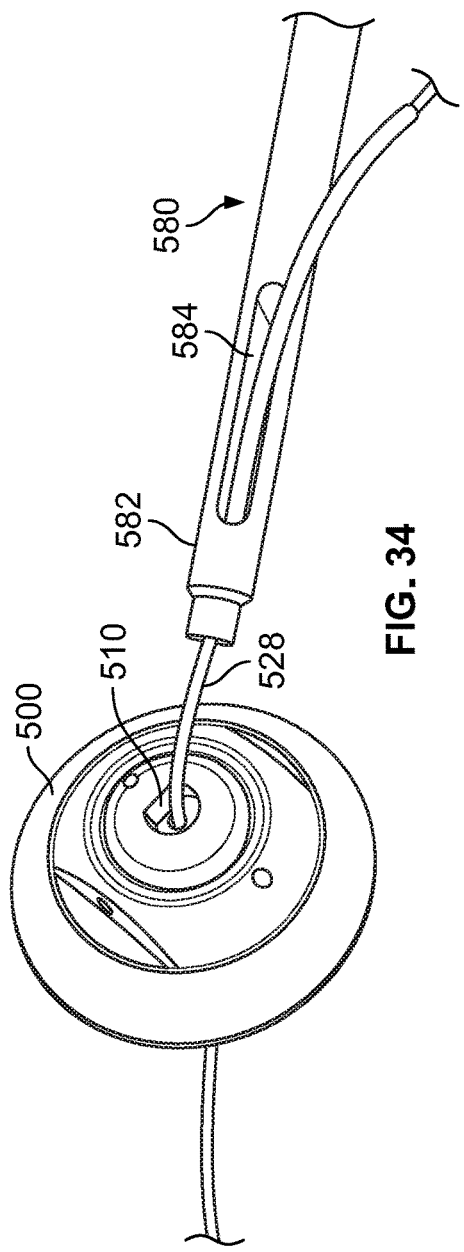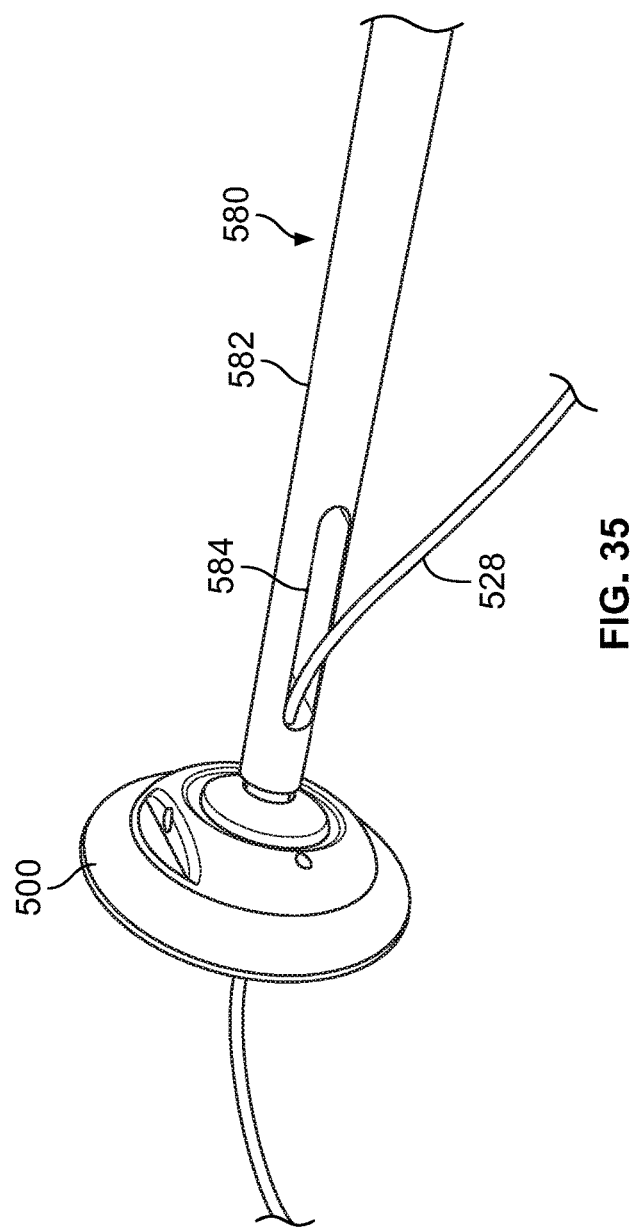

DEVICES AND METHODS FOR POSITIONING AND MONITORING TETHER LOAD FOR PROSTHETIC MITRAL VALVE

CROSS-REFERENCE TO RELATED APPLICATIONS

This application is a continuation of International Application No. PCT/US2015/019418, filed Mar. 9, 2015, which claims priority to and the benefit of U.S. Provisional Patent Application No. 61/950,429, filed Mar. 10, 2014, entitled "Devices and Methods for Monitoring Tether Load for Prosthetic Mitral Valve," U.S. Provisional Patent Application No. 61/970,887, filed Mar. 26, 2014, entitled "Post-Deployment Adjustment of a Prosthetic Mitral Valve," and U.S. Provisional Patent Application No. 61/970,882, filed Mar. 26, 2014, entitled "Post-Deployment Adjustment of a Prosthetic Mitral Valve." The disclosure of each of the foregoing applications is incorporated herein by reference in its entirety.

BACKGROUND

Embodiments are described herein that relate to devices and methods for anchoring medical device such as a prosthetic heart valve replacement, and more particularly to devices and methods for the post-deployment adjustment and/or re-positioning of such a medical device.

Some known prosthetic heart valves, such as prosthetic mitral valves, include one or more tethers that extend from the valve to the exterior of the heart, and are secured to an outer ventricular wall of the heart with an epicardial anchor device. During such procedures, positioning the anchor device and providing a desired tension to the securing tether can be challenging. Many known devices do not have the ability to make adjustments to the anchor device or to the tension of the tether after initial placement. Further, known devices do not have the ability to measure and monitor the tension on the tether during deployment of the valve to assist in providing an optimal tension and position.

Some problems associated with improper tensioning of a securing tether can include, for example, the tether becoming progressively slack over time, a tether which has been overtightened and is deforming the positioning of the deployed valve, and a tether which has been deployed in a less than optimal angular configuration or has migrated such that the valve axis is no longer orthogonal to the plane of the native valve's annulus.

Accordingly, there is a need for devices and methods for adjusting and/or repositioning a prosthetic heart valve after its initial deployment and for monitoring the tension on a securing tether extending from the prosthetic heart valve.

SUMMARY

Apparatus and methods are described herein for positioning an epicardial anchor device and measuring the load of a tether extending from a prosthetic heart valve and coupled to the epicardial anchor device. In some embodiments, an apparatus includes a handle assembly coupled to an elongate member and a docking member coupled to a distal end of the elongate member. The docking member can be releasably coupled to an epicardial anchor device configured to secure a tether extending from a prosthetic heart valve implanted with a heart at a location on an exterior of a ventricular wall of the heart. A force sensor device is coupled to the handle assembly and can measure a force exerted on the force sensor device. The force is associated with a tension of the tether extending through the elongate member, handle assembly and force sensor device.

BRIEF DESCRIPTION OF THE DRAWINGS

FIG. 16A is a perspective view and FIG. 16B is a top view of a portion of the positioning device of FIG. 13.

FIG. 18 is a top view of a positioning device, according to another embodiment.

FIG. 19 is a perspective view of a portion of the positioning device of FIG. 18 shown partially exploded.

FIG. 28 is a perspective view of a portion of the force sensor device of FIG. 26.

FIG. 30 is a side view of the positioning device of FIG. 22.

FIG. 31 is a partial cross-sectional side view of a tension limiting device according to an embodiment.

FIG. 34 is a perspective view of a portion of the tether release tool of FIG. 32 shown being coupled to an epicardial anchor device.

FIG. 35 is a perspective view of a portion of the tether release tool of FIG. 32 shown coupled to the epicardial anchor device of FIG. 34.

DETAILED DESCRIPTION

Figure 1:
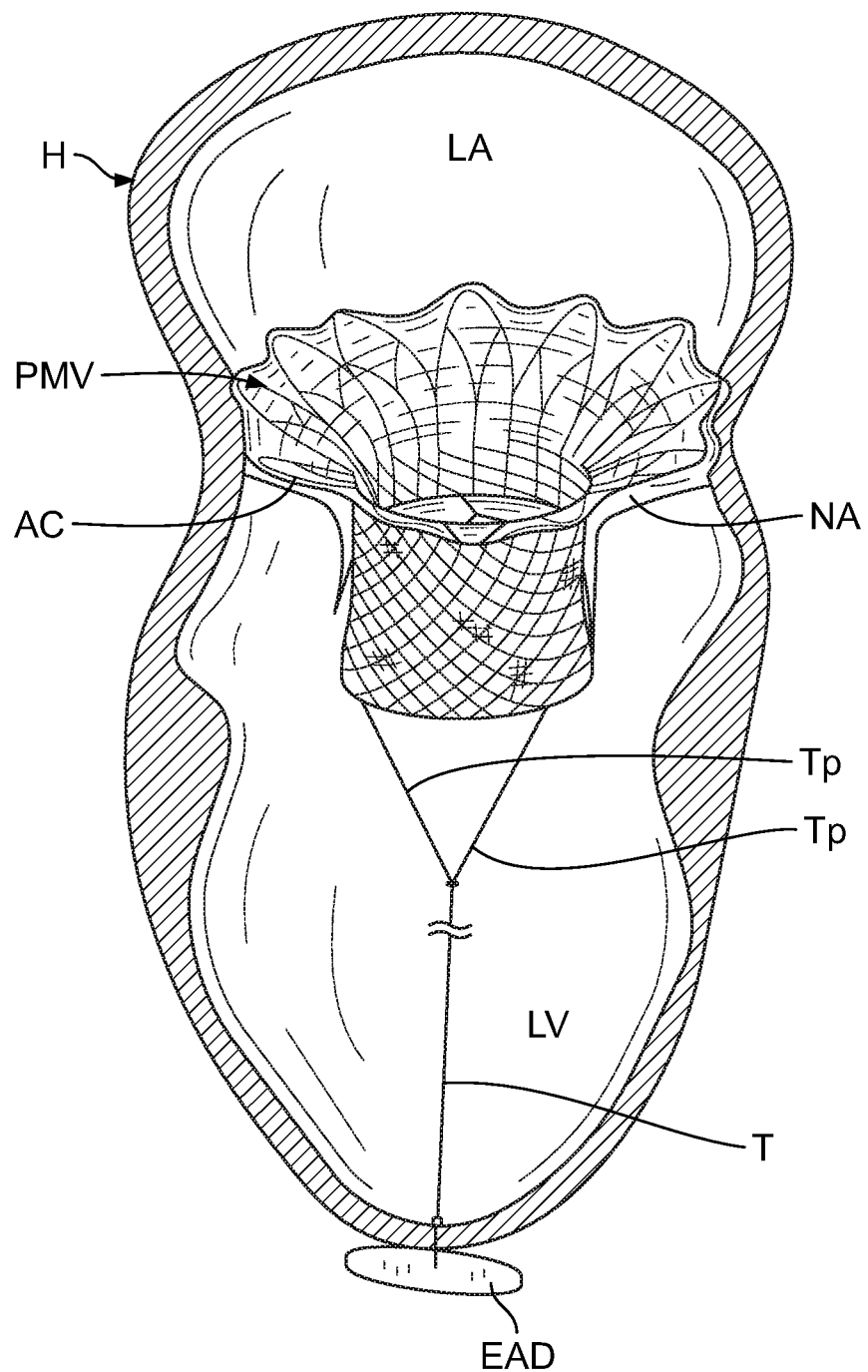
FIG. 1 is a schematic cross-sectional illustration of portion of a heart with a prosthetic mitral valve implanted therein and an epicardial anchor device anchoring the mitral valve in position.

Apparatus and methods are described herein that can be used for the post-deployment adjustment and/or re-positioning of a transcatheter prosthetic heart valve, such as a mitral valve, that has been deployed into the annulus of a native valve, such as a mitral valve. For example, such a prosthetic mitral valve can be anatomically secured in a two-phase process that includes securing the prosthetic mitral valve in the native annulus using an atrial cuff and a tether axial tensioning system in combination with a laterally expanded stent, and to methods for making such systems.

In some embodiments, apparatus and methods are described herein for monitoring the tension applied to a securing tether extending from a prosthetic mitral valve that has been deployed into the native mitral valve.

Various embodiments described herein address problems concerning valve delivery and deployment, valve compliance, perivalvular leaking, hemodynamic issues such as left ventricular outflow tract (LVOT) interference, clotting, cardiac remodeling, etc.

In some embodiments, an adjustable tether and epicardial anchor device for a compressible prosthetic heart valve replacement are described herein, which can be deployed into a closed beating heart using, for example, a transcatheter delivery system. In some embodiments, such a valve replacement device can be deployed in a minimally invasive fashion and by way of example considers a minimally invasive surgical procedure utilizing the intercostal or sub-xyphoid space for valve introduction. To accomplish this, the valve is formed so that it can be compressed to fit within a delivery system and then ejected from the delivery system into the target location, for example, the annulus of the mitral or tricuspid valve.

In some embodiments, there is provided a method of adjusting the length and/or tension of a tether for a tethered transcatheter prosthetic heart valve after a transcatheter valve implantation procedure in a patient. Such a method can include adjusting the transluminal length of a ventricular tether, wherein the tether is anchored between an epicardial anchor device that is releasably affixed to an external epicardial surface of the heart and a valve-based fastening system on a transcatheter prosthetic heart valve that is deployed in the native valve annulus of the patient. Upon releasing the tether from the epicardial anchor device, the tether length and/or tension is adjusted and the tether is re-fastened to the epicardial anchor device.

In another embodiment, there is provided a method as above, further including capturing the tether, threading the tether through a tether release tool, re-engaging the tether release tool with the epicardial anchor device, unlocking the pin and releasing the tether. In some embodiments, after adjusting the length of the tether (longer or shorter), the tether tensioning force can be measure again, and then the tether can be re-pinned into the epicardial anchor device.

In some embodiments, there is provided a device for adjusting the length and/or tension of a tether for a tethered transcatheter prosthetic heart valve after a transcatheter valve implantation procedure in a patient. The device can include a positioning device for operatively engaging an epicardial anchor device, and the positioning device includes a positioning rod. The positioning rod member includes at a distal end of an elongate member a docking member that has a hinged frame that is connected to a circular platform having two bent locking tines or flanges located across from each other. The elongate member may or may not be hollow and includes a mechanism associated therewith for inserting or withdrawing a locking pin from a tether. The positioning device further includes a pin locking thumb wheel sub-component to actuate the pin locking mechanism that drives or removes a piercing pin on the epicardial anchor device into or from the tether. The positioning device further includes a transparent segment between the pin locking thumb wheel and a proximal end of the positioning device. The transparent segment has an implant position scale marked thereon. A proximal end of the positioning device also has a tether attachment pin vise. When the tether is threaded through the epicardial anchor device and the positioning device, and when the tether is drawn/pulled to the desired tension, e.g., such that the deployed valve seats firmly in the native annulus and any regurgitation seen on fluoroscopy or echocardiography is no longer present, the tether tensioning can be adjusted by visually observing the tether within the transparent segment of the positioning device and comparing the longitudinal distance travelled against an implant position scale. After the tether is suitably located, the pin locking thumb wheel is actuated and the pin locks the tether in place on the epicardial anchor device. The docking member is then disengaged from the epicardial anchor device.

In some embodiments, there is provided a tether release tool that has a distal tip that includes a shaped anchor device-engagement tip, a distal opening and a passageway in fluid communication with an angled tether capture/recapture access port. The angled tether capture/recapture access port allows a tether to be captured and released from a locked position, and the shaped anchor device-engagement tip is configured to fit within a similarly shaped portion of an epicardial anchor device.

In some embodiments, there is provided a method of tethering a prosthetic heart valve during a transcatheter valve replacement procedure that includes deploying a transcatheter prosthetic heart valve in a patient using as an anchor an adjustable tether that is anchored within the heart between an apically affixed epicardial anchor device and a stent-based fastening system (e.g., attached to the prosthetic heart valve). The transcatheter prosthetic heart valve includes an expandable tubular stent having a cuff and an expandable internal leaflet assembly. The cuff includes wire covered with stabilized tissue or synthetic material, and the leaflet assembly is disposed within the stent and includes stabilized tissue or synthetic material.

In some embodiments, an epicardial anchor device for anchoring a transluminal (transventricular) suture/tether includes a substantially rigid suturing disk having a tether-capture mechanism such as an axial tunnel, a winding channel, or a functional equivalent, and a tether locking mechanism such as a locking pin or screw that intersects the axial tunnel, a locking pin or screw operatively associated with the winding channel, a cam device like a rope lock that grips the tether by compression between two cams or a cam and fixed locking wall, a metal compression fastener, a tooth and pawl device, various combinations of the above, or a functional equivalent thereof.

In another embodiment, an epicardial anchor device for anchoring a transluminal suture includes a substantially rigid suturing disk having an axial tunnel, a locking pin locking pin tunnel that intersects the axial tunnel, a locking pin operatively associated with the locking pin tunnel, one or more radial channels that do not intersect with the axial tunnel and that do not intersect the locking pin tunnel, and a winding channel circumferentially disposed within a perimeter sidewall of the disk.

In some embodiments, an epicardial anchor device further includes a polyester velour coating. In some embodiments, the one or more radial channels include four radial channels. In some embodiments, the one or more radial channels each have an enlarged axial keyhole tunnel.

In some embodiments, an epicardial anchor device includes a flexible pad operatively associated with the rigid tethering/suturing disk, and the flexible pad has a through-hole longitudinally aligned with the axial tunnel. In some embodiments, the epicardial anchor device further includes a sleeve gasket operatively associated with the rigid tethering/suturing disk, and the sleeve gasket has a lumen longitudinally aligned with the axial tunnel. In some embodiments, the device further includes a sleeve gasket attached to the rigid tethering/suturing disk and a flexible pad attached to the sleeve gasket. In such an embodiment, the sleeve gasket has a lumen longitudinally aligned with the axial tunnel of the tethering/suturing disk, and the flexible pad has a through-hole longitudinally aligned with both the lumen of the sleeve gasket and the axial tunnel of the tethering/suturing disk.

In some embodiments, a device for anchoring a transluminal tethering/suture includes a substantially rigid tethering/suturing disk, a sleeve gasket connected to the tethering/suturing disk, and a flexible pad connected to the sleeve gasket. The substantially rigid tethering/suturing disk has an axial tunnel, a locking pin tunnel that intersects the axial tunnel, a locking pin operatively associated with the locking pin tunnel, one or more radial channels that do not intersect with the axial tunnel and that do not intersect the locking pin tunnel, and a winding channel circumferentially disposed within a perimeter sidewall of the disk. The sleeve gasket is in longitudinal alignment with the axial tunnel, and the flexible pad has a through-hole longitudinally aligned with both the lumen of the sleeve gasket and the axial tunnel of the tethering/suturing disk.

In another embodiment, an epicardial anchor device for anchoring a transluminal suture includes a substantially rigid tethering/suturing disk having an axial tunnel, a locking pin tunnel that intersects the axial tunnel, and a locking pin operatively associated with the locking pin tunnel.

In some embodiments, a method for anchoring a transluminal suture includes affixing a transluminal suture to an epicardial anchor device as described herein, and positioning the epicardial anchor device external to a body lumen. The transluminal tether/suture extends from within the lumen to the epicardial anchor device.

In another embodiment, a tether and epicardial anchor device as described herein further includes a tether tension load measuring device operatively associated with the tether. In some embodiments, a tension sensor includes one or more electronic strain gage transducers. The tension sensor can be configured for dynamic tension, static tension, or both dynamic and static tension measurement. In some embodiments, the tether is loaded with a specific tension, such as, for example, 1.0 to 4.0 lbs.

In another embodiment, there is provided a device and exemplary method for monitoring and/or controlling tether load during implant positioning using a fluid chamber device described in more detail below. A force sensor device having an annular fluid chamber is installed on the proximal end of a positioning device. This chamber is connected to a pressure transducer and then connected to a monitoring display. In some embodiments, a mechanical indicator can be used in conjunction therewith. A spring device may be connected to a mechanical tension meter to show load range. In some embodiments, the force sensor device remains as an integral part of the epicardial fastening pad assembly and is not removed after the tether tensioning is performed.

In some embodiments, a sterile surgical kit can be provided. The sterile surgical kit can contain a transcatheter delivery system, an epicardial anchor device and/or a transcatheter prosthetic valve.

In another embodiment, there is provided method of treating mitral or tricuspid regurgitation in a patient, which includes surgically deploying an adjustable-tethered prosthetic heart valve into the mitral or tricuspid annulus of the patient.

In another embodiment, the space between the cuff tissue and cuff Dacron liner (inside-outside) may be used to create a cuff that is expandable, swellable or may be inflated, and which provides an enhanced level of sealing of the cuff against the annular tissue.

Various embodiments described herein address problems concerning valve delivery and deployment, valve compliance, perivalvular leaking, hemodynamic issues such as LVOT interference, clotting, cardiac remodeling and so forth.

In some embodiments described herein, a tethering system for a prosthetic mitral valve is provided that is designed to maintain integrity to about 800 million cycles, or about 20 years. The use of a compressible prosthetic valve delivered via transcatheter endoscope techniques addresses various delivery issues. Deployment is addressed through the use of a prosthetic valve having a shape that features a tubular stent body that contains leaflets and an atrial cuff. This allows the valve to seat within the mitral annulus and be held by the native mitral leaflets. The use of a flexible valve attached using an apical tether provides compliance with the motion and geometry of the heart. The geometry and motion of the heart are well-known as exhibiting a complicated biphasic left ventricular deformation with muscle thickening and a sequential twisting motion. The additional use of the apically secured ventricular tether helps maintain the prosthetic valve's annular position without allowing the valve to migrate, while providing enough tension between the cuff valve annulus to reduce and eliminate perivalvular leakage. The use of an adjustable tether or an adjustable paired-tether that is attached to an apical location can reduce or eliminate the cardiac muscle remodeling that has been witnessed in prior art devices. Some prior art devices can have a problem with unwanted change in tissue at the anchoring locations, as well as heart-generated migration of the original anchoring locations to new locations that reduce or destroy the prior art valve's effectiveness. The use of a compliant valve prosthesis and the special shape and features help reduce or eliminate clotting and hemodynamic issues, including LVOT interference problems. Many prior art valves were not designed with an awareness of, or were not able to address, problems with blood flow and aorta/aortic valve compression issues.

Structurally, a prosthetic heart valve as used with the apparatus and methods described herein can include a self-expanding tubular body having a cuff at one end and one or more tethers attached at the other end. Disposed within the tubular body is a leaflet assembly that contains the valve leaflets, and the valve leaflets can be formed from stabilized tissue or other suitable biological or synthetic material. In one embodiment, the leaflet assembly may include a wire form where a formed wire structure is used in conjunction with stabilized tissue to create a leaflet support structure which can have anywhere from 1, 2, 3 or 4 leaflets, or valve cusps disposed therein. In another embodiment, the leaflet assembly is wireless and uses only the stabilized tissue and stent body to provide the leaflet support structure, without using wire, and which can also have anywhere from 1, 2, 3 or 4 leaflets, or valve cusps disposed therein.

The upper cuff portion may be formed by heat-forming a portion of a tubular Nitinol® braided (or similar) stent such that the lower portion retains the tubular shape, but the upper portion is opened out of the tubular shape and expanded to create a widened collar structure that may be shaped in a variety of functional regular or irregular funnel-like or collar-like shapes. In one embodiment, the entire structure is formed from a laser-cut stent and collar design, as described further herein As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to a direction closer to and away from, respectively, an operator of, for example, a medical device. Thus, for example, the end of the medical device closest to the patient's body (e.g., contacting the patient's body or disposed within the patient's body) would be the distal end of the medical device, while the end opposite the distal end and closest to, for example, the user (or hand of the user) of the medical device, would be the proximal end of the medical device.

A prosthetic mitral valve can be anchored to the heart at a location external to the heart via one or more tethers coupled to an anchor device, as described herein. For example, the tether(s) can be coupled to the prosthetic mitral valve and extend out of the heart and be secured at an exterior location (e.g., the epicardial surface) with an anchor device, as described herein. An anchor device as described herein can be used with one or more such tethers in other surgical situations where such a tether may be desired to extend from an intraluminal cavity to an external anchoring site. Various different types and/or configurations of an anchor device (also referred to herein as "epicardial anchor device" or "epicardial pad" or "pad") can be used to anchor a prosthetic mitral valve in the methods described herein. For example, any of the epicardial anchor devices described in PCT International Application No. PCT/US2014/049218, filed Jul. 31, 2014, entitled "Epicardial Anchor Devices and Methods," (referred to herein as "the '218 PCT application"), the disclosure of which is incorporated herein by reference in its entirety, can be used.

FIG. 1 is a schematic cross-sectional illustration of the left ventricle LV and left atrium LA of a heart H having a transcatheter prosthetic mitral valve PMV deployed therein and an epicardial anchor device EAD as described herein securing the prosthetic mitral valve PMV in place. FIG. 1 illustrates the prosthetic mitral valve PMV seated into the native valve annulus and held there using an atrial cuff AC of the prosthetic mitral valve PMV and a ventricular tether T secured with attachment portions Tp to the prosthetic mitral valve PMV and to the epicardial anchor EAD. The epicardial anchor device EAD can be various different shapes, sizes, types and configurations, for example, the EAD can be an epicardial anchor device such as those described in the '218 PCT application incorporated by reference above. Further, the prosthetic mitral valve PMV and the tether T can be, for example, a prosthetic mitral valve and tether, respectively, as described in the '218 PCT application or other suitable types and configurations.

Figure 2:
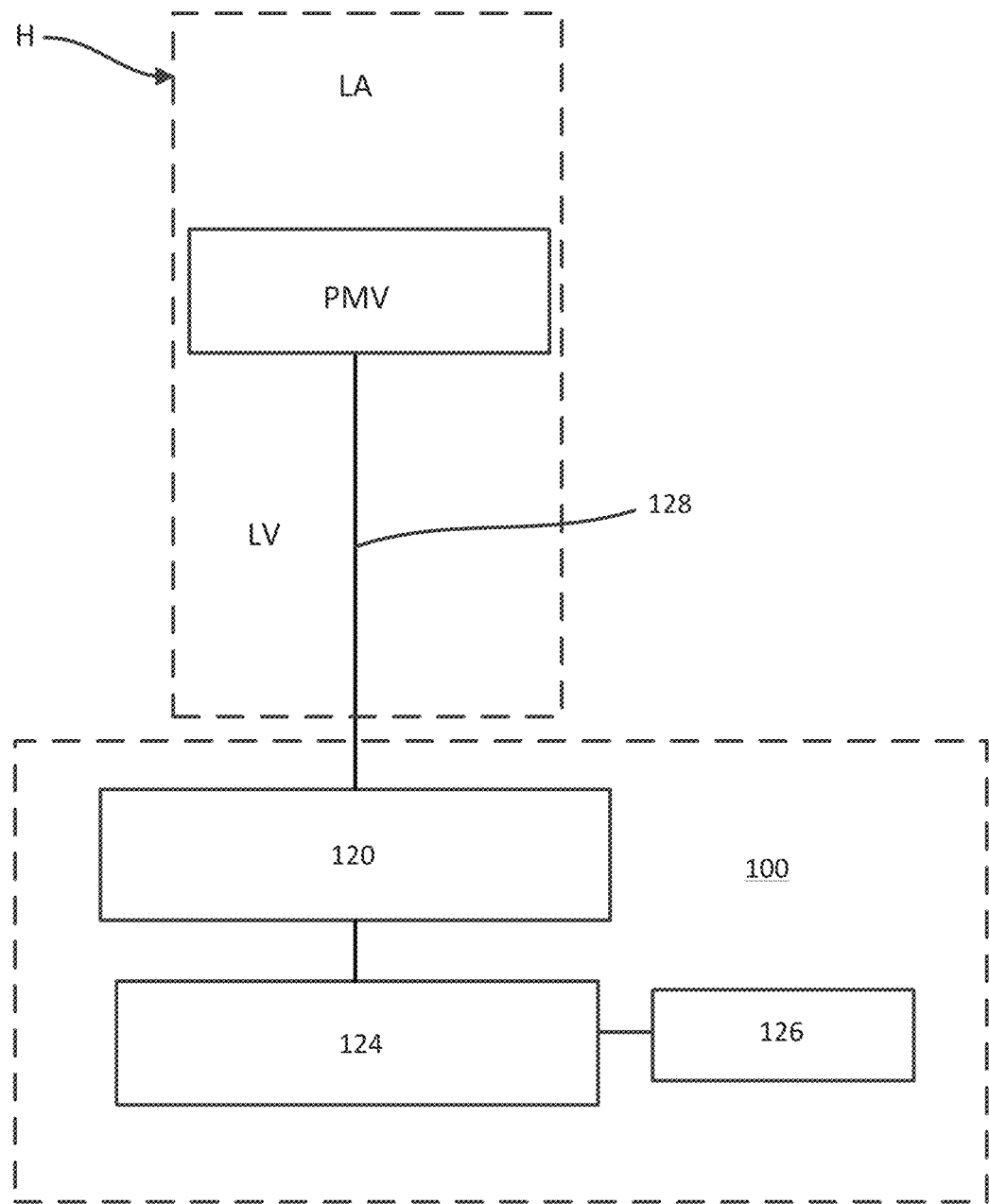
FIG. 2 is a schematic illustration of an epicardial anchor device, according to an embodiment.

FIG. 2 is a schematic illustration of an epicardial anchor device 100 (also referred to herein as "anchor device" or "epicardial anchor") according to an embodiment. The anchor device 100 can be used to anchor or secure a prosthetic mitral valve PMV deployed between the left atrium LA and left ventricle LV of a heart H. The anchor device 100 can be used, for example, to anchor or secure the prosthetic mitral valve PMV via a suturing tether 128 as described above with respect to FIG. 1. The anchor device 100 can also seal a puncture formed in the ventricular wall (not shown in FIG. 2) of the heart during implantation of the prosthetic mitral valve PMV. The anchor device 100 can also be used in other applications to anchor a medical device (such as any prosthetic atrioventricular valve or other heart valve) and/or to seal an opening such as a puncture.

The anchor device 100 can include a pad (or pad assembly) 120, a tether attachment member 124 and a locking pin or locking pin assembly 126. The pad 120 can contact the epicardial surface of the heart and can be constructed of any suitable biocompatible surgical material. The pad 120 can be used to assist the sealing of a surgical puncture formed when implanting a prosthetic mitral valve.

In some embodiments, the pad 120 can be made with a double velour material to promote ingrowth of the pad 120 into the puncture site area. For example, pad or felt pledgets can be made of a felted polyester and may be cut to any suitable size or shape, such as those available from Bard® as PTFE Felt Pledgets having a nominal thickness of 2.87 mm. In some embodiments, the pad 120 can be larger in diameter than the tether attachment member 124. The pad 120 can have a circular or disk shape, or other suitable shapes.

The tether attachment member 124 can provide the anchoring and mounting platform to which one or more tethers 128 can be coupled (e.g., tied or pinned). The tether attachment member 124 can include a base member (not shown) that defines at least a portion of a tether passageway (not shown) through which the tether 128 can be received and pass through the tether attachment member 124, and a locking pin channel (not shown) through which the locking pin 126 can be received. The locking pin channel can be in fluid communication with the tether passageway such that when the locking pin 126 is disposed in the locking pin channel, the locking pin 126 can contact or pierce the tether 128 as it passes through the tether passageway as described in more detail below with reference to specific embodiments.

The locking pin assembly 126 can be used to hold the tether 128 in place after the anchor device 100 has been tightened against the ventricular wall and the tether 128 has been pulled to a desired tension. For example, the tether 128 can extend through a hole in the pad 120, and through the tether passageway of the tether attachment member 124. The locking pin 126 can be inserted or moved within the locking pin channel 134 such that it pierces or otherwise engages the tether 128 as the tether 128 extends through the tether passageway of the tether attachment member 124. Thus, the locking pin 126 can intersect the tether 128 and secure the tether 128 to the tether attachment member 124.

The tether attachment member 124 can be formed with, a variety of suitable biocompatible material. For example, in some embodiments, the tether attachment member 124 can be made of polyethylene, or other hard or semi-hard polymer, and can be covered with a polyester velour to promote ingrowth. In other embodiments, the tether attachment member 124 can be made of metal, such as, for example, Nitinol®, or ceramic materials. The tether attachment member 124 can be various sizes and/or shapes. For example, the tether attachment member 124 can be substantially disk shaped.

In use, after a PMV has been placed within a heart, the tether extending from the PMV can be inserted into the tether passageway of the anchor device 100 and the tension on the tether attachment device can be adjusted to a desired tension. Alternatively, in some cases, the tether extending from the PMV can be coupled to the anchor device 100 prior to the PMV being placed within the heart. The anchor device 100 (e.g., some portion of the anchor device such as the tether attachment member 124, or the lever arm or hub depending on the particular embodiment) can be actuated such that the locking pin 126 intersects the tether passageway and engages a portion of the tether disposed within the tether passageway, securing the tether to the tether attachment member. In some embodiments, prior to inserting the tether into the tether passageway, the anchor device 100 can be actuated to configure the anchor device 100 to receive the tether. For example, if the tether attachment member includes a lever arm movably coupled to the base member, the lever arm may need to be moved to an open position to allow the tether to be inserted. In some embodiments, the anchor device 100 can be actuated by rotating a hub relative to a base member of the tether attachment member 124 such that the locking pin 126 is moved from a first position in which the locking pin is spaced from the tether passageway and a second position in which the locking pin intersects the tether passageway and engages or pierces the portion of the tether.

Figure 3:
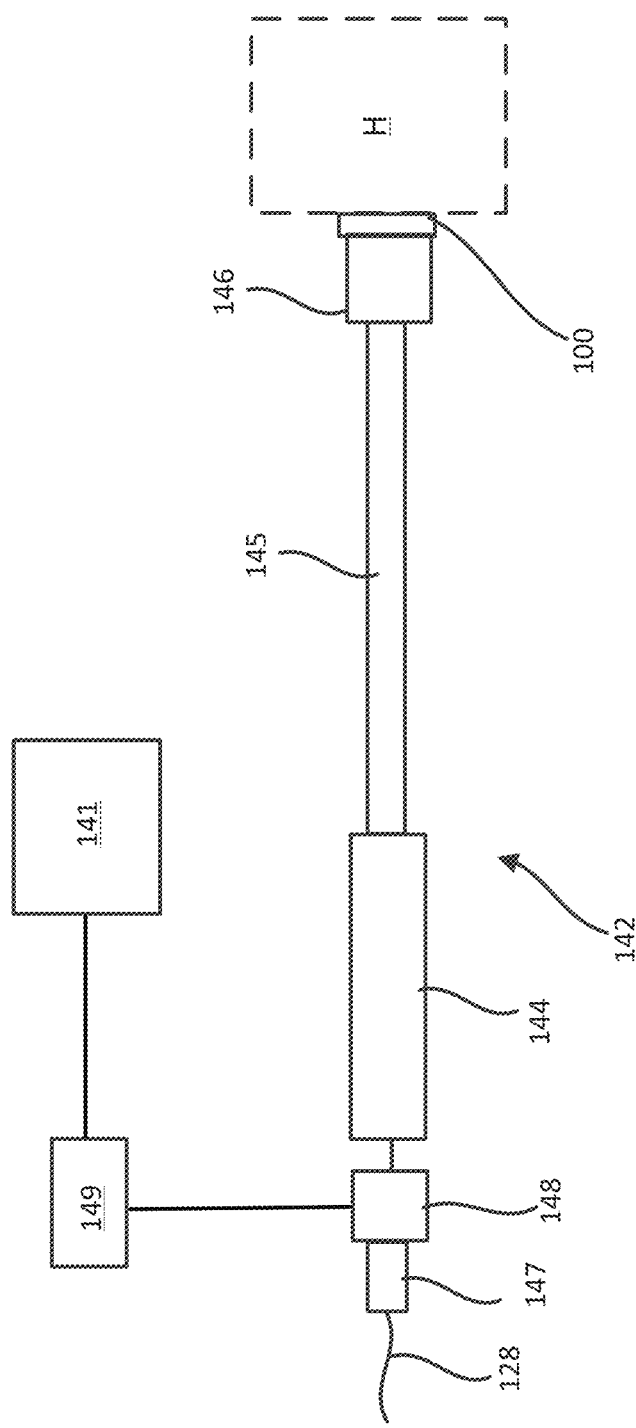
FIG. 3 is a schematic illustration of a positioning device, according to an embodiment.
Figure 4:
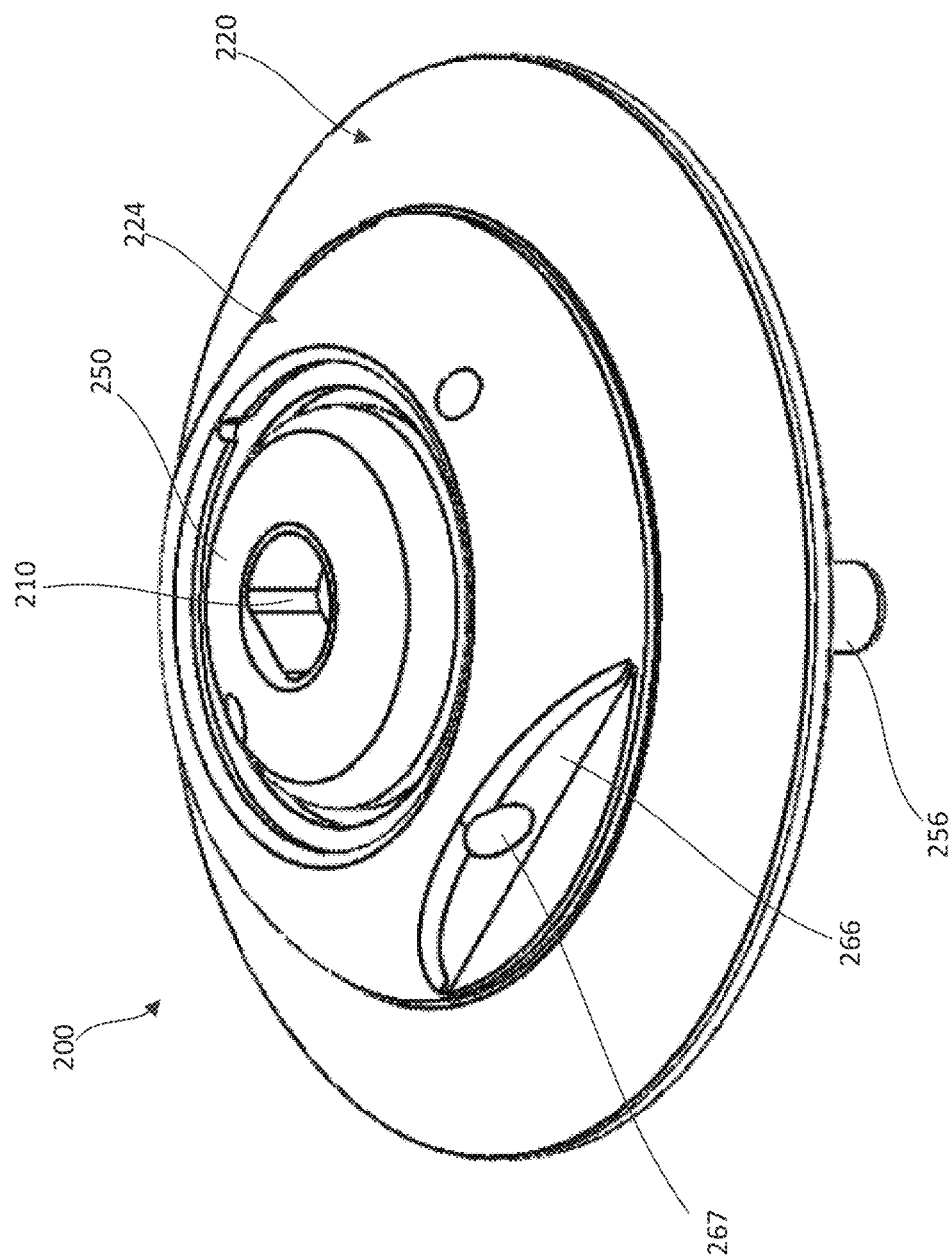
FIG. 4 is a top perspective view of an epicardial anchor device, according to another embodiment.
Figure 5:
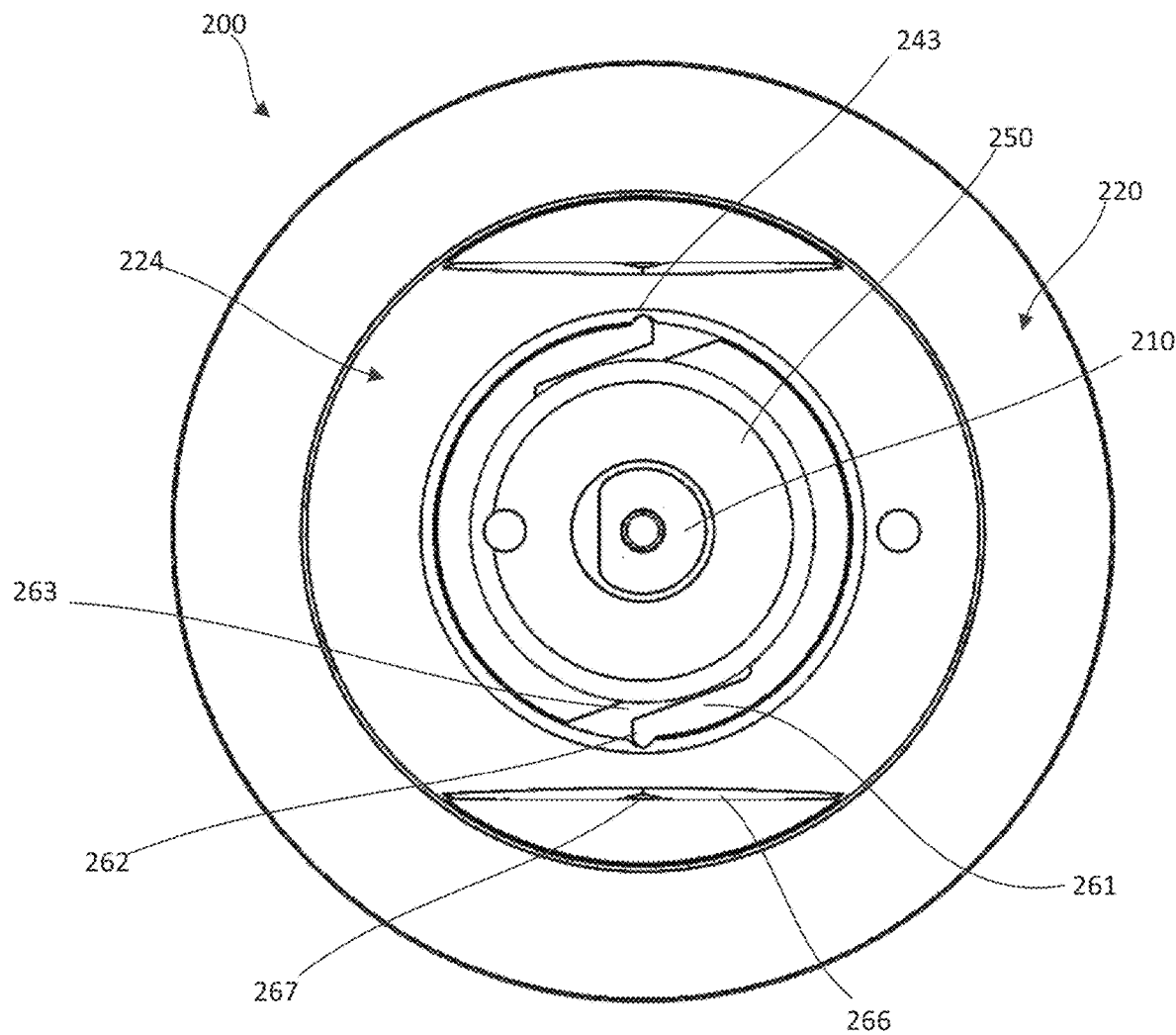
FIG. 5 is a top view of the epicardial anchor device of FIG. 4.
Figure 6:
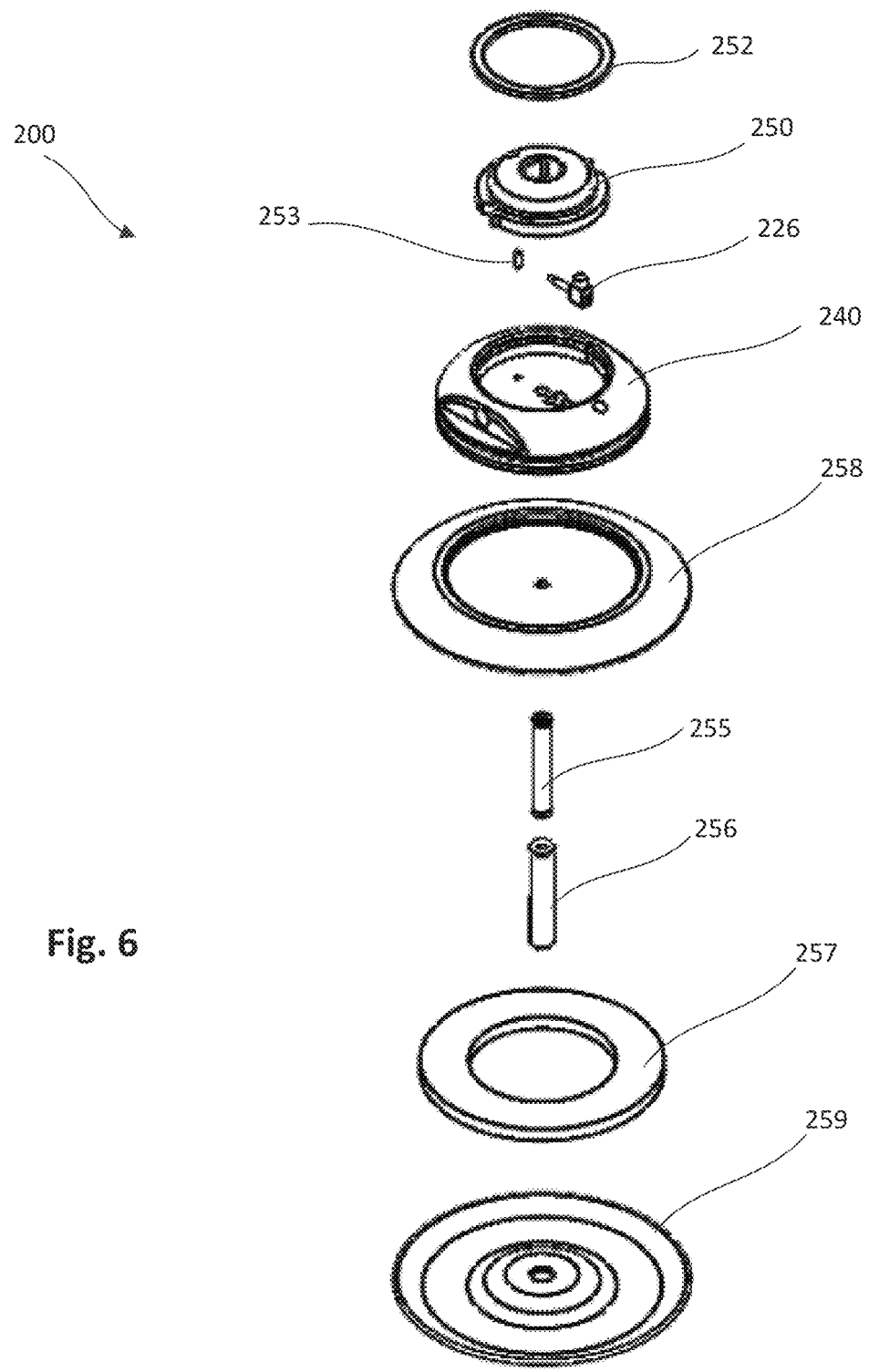
FIG. 6 is an exploded view of the epicardial anchor device of FIG. 4.

FIG. 3 is a schematic illustration of an embodiment of a positioning device 142 that can be used to position the epicardial anchor device 100 and measure the tension applied to a tether 128 attached to a prosthetic mitral valve (not shown in FIG. 3) to be anchored by the epicardial anchor device 100. The positioning device 142 includes a handle assembly 144, an elongate member 145, a docking member 146, and a tether securing member 147. In some embodiments, the positioning device 142 can include a force sensor device 148, which can communicate with a transducer 149, which in turn can communicate with an electronic device 141 to display the output of the force sensor device 148. In some embodiments, the transducer 149 can be incorporated within the force sensor device 148. In some embodiments, the force sensor device 148 can be coupled to a data acquisition module rather than a transducer. The electronic device 141 can be, for example, a monitor or display of a computer, such as a laptop computer or a desktop computer, or a handheld electronic device such as a tablet, phone or other electronic device configured to receive and display the output of the force sensor device 148.

The positioning device 142 can include other various components that can be for example coupled to or incorporated within the handle assembly 144 or another component of the positioning device 142. The docking member 146 can be used to releasably couple the epicardial pad 100 to the positioning device 142 and can be actuated by one or more components of the positioning device 142. The tether securing device 147 can include, for example, a vice mechanism used to lock the tether 128 at a desired position. In some embodiments, the tether securing device 147 can include a pinning device that can pierce the tether 128 to secure the tether 128 in the desired position. More detailed descriptions of various components of embodiments of a positioning device 142 are described below.

FIGS. 4-12 illustrate an epicardial anchor device according to an embodiment. An epicardial anchor device 200 includes a tether attachment member 224, a pad assembly 220, a tube member 255 and a tube cover member 256. The tether attachment member 224 includes a base member 240, a hub 250, a retaining ring 252, a locking pin assembly 226, and a pin member 253. The locking pin assembly 226 includes a driver portion 246 and a piercing portion 249. The base member 940 defines a circumferential pad channel 242, a retaining channel 251 and a locking pin channel 234. The pad channel 242 can be used to couple the pad assembly 220 to the tether attachment member 224. The retaining channel 251 can receive an outer edge of the retaining ring 252, which is used to retain the hub 250 to the base member 240. The base member 240 also defines cutouts or detents 243, as shown for example, in FIGS. 5, 7 and 12.

The tube member 255 is coupled to the base member 240 and the base member 240, the hub 250 and the tube member 255 collectively define a tether passageway 235 through which a tether (not shown) can be received. The cover member 256 can be formed with a fabric material, such as for example, Dacron®. The tether channel 235 intersects the locking pin channel 234 and is in fluid communication therewith.

The pad assembly 220 includes a top pad portion 258, a bottom pad portion 259 and a filler member 257 disposed therebetween. The top pad portion 258 and the bottom pad portion 259 can each be formed with, for example, a flexible fabric material. The top pad portion 258 and the bottom pad portion 259 can each define a central opening through which the tube member 255 can pass through. A portion of the top pad portion 258 is received within the channel 242 of the base member 240 as shown, for example, in FIGS. 7-9.

Figure 7:
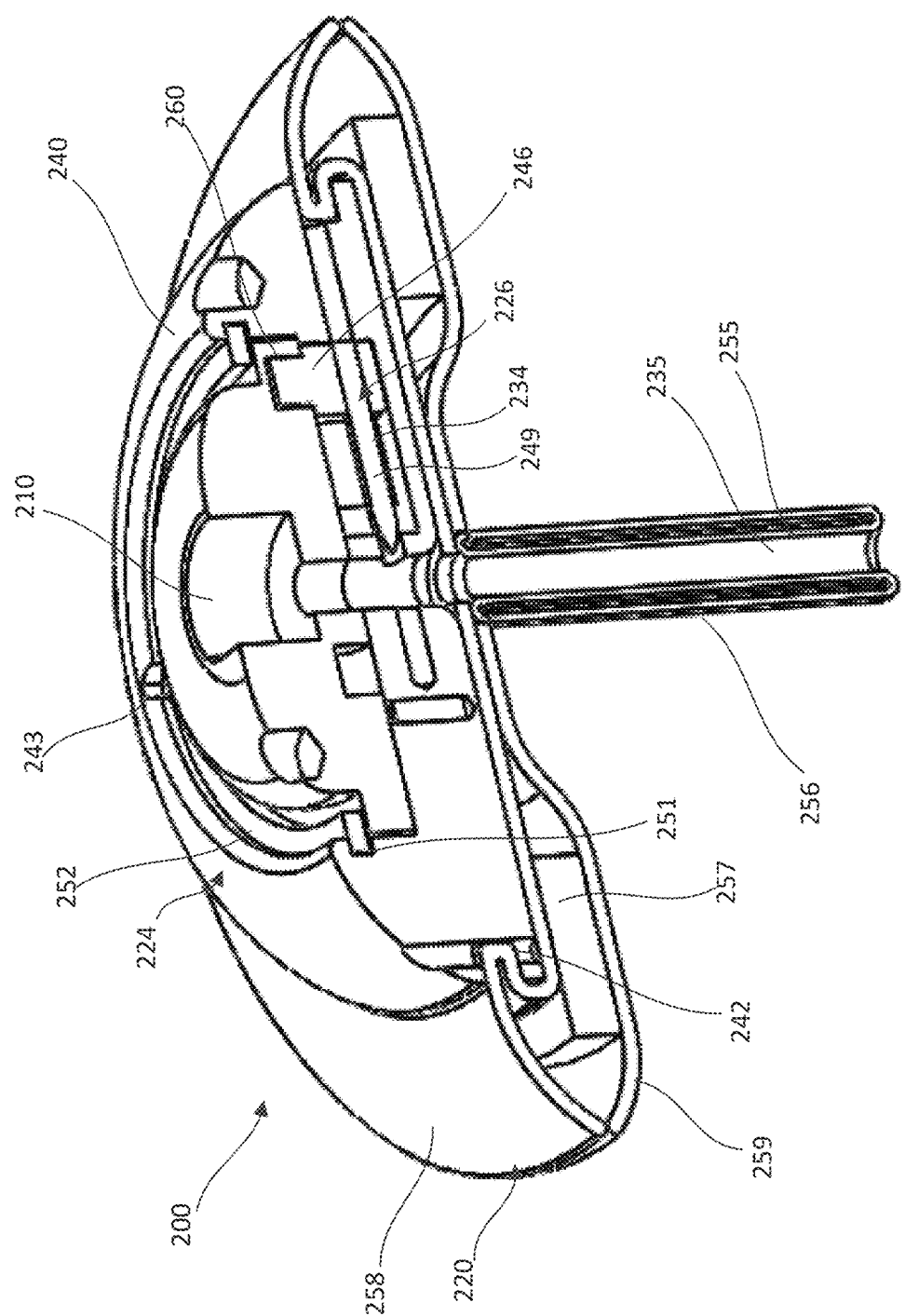
FIG. 7 is a cross-sectional perspective view of the epicardial anchor device of FIG. 4 with a locking pin of the device shown in a first position.
Figure 8:
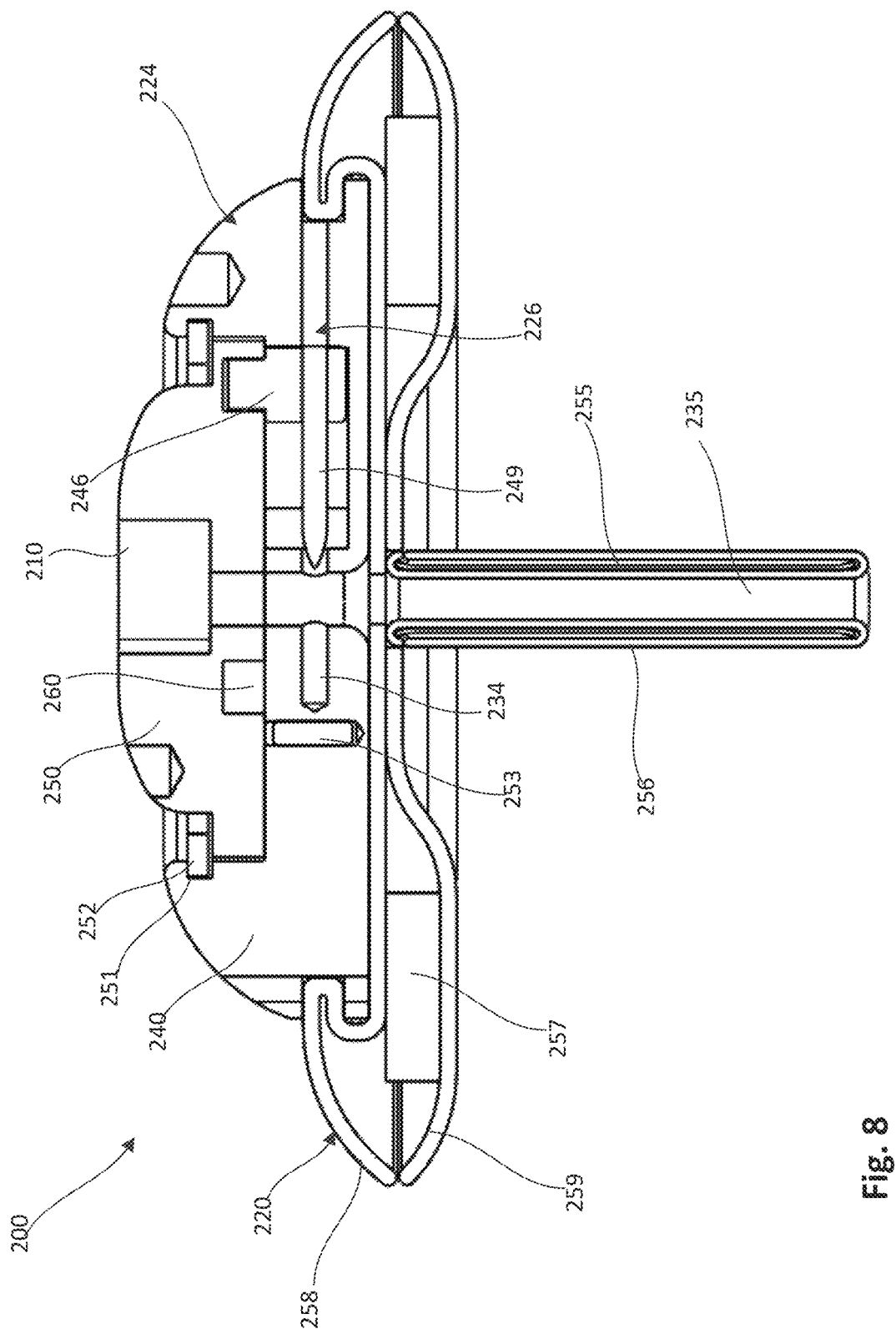
FIG. 8 is a cross-sectional side view of the epicardial anchor device of FIG. 4 with the locking pin of the device shown in the first position.
Figure 9:
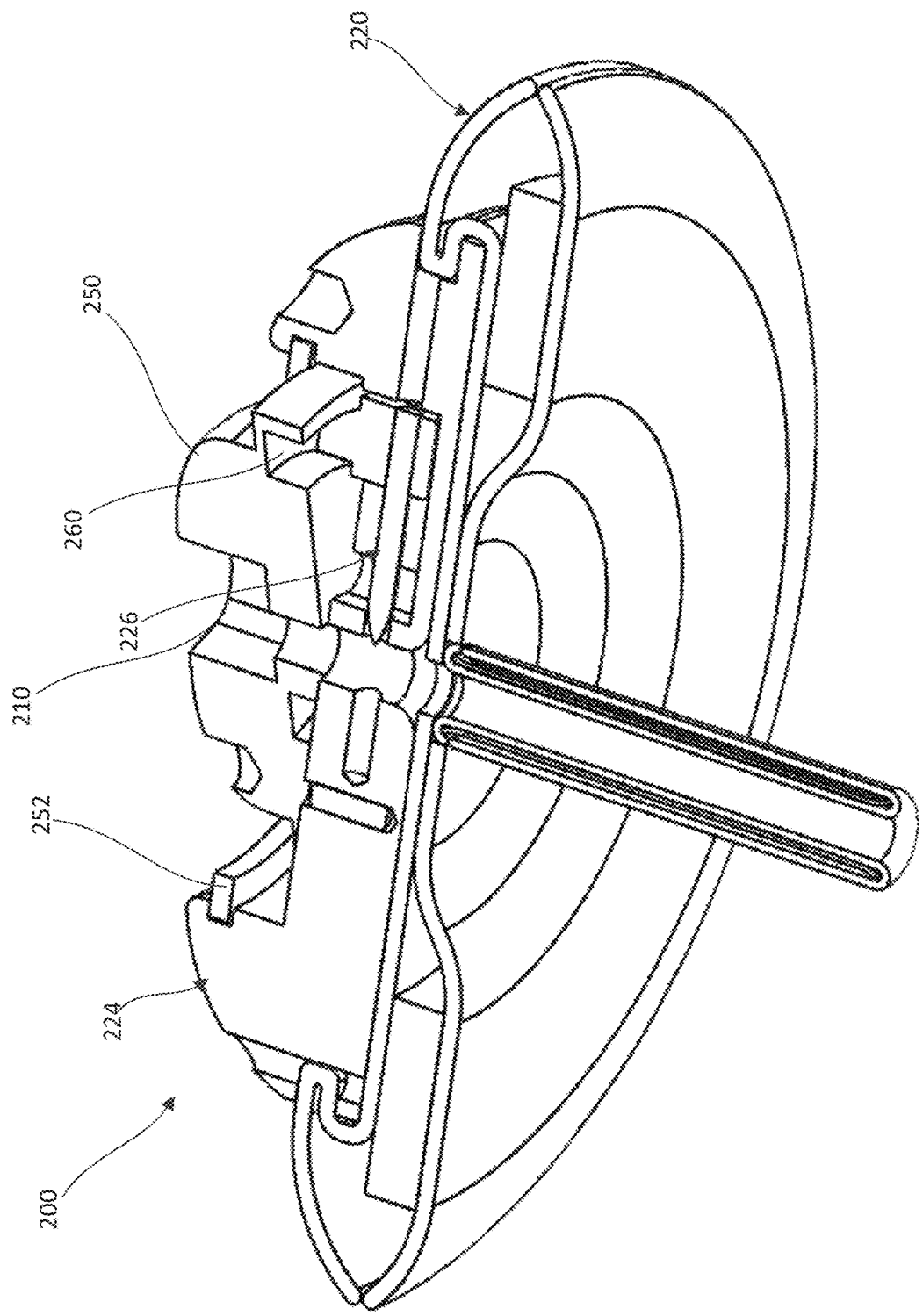
FIG. 9 is a cross-sectional bottom perspective view of the epicardial anchor device of FIG. 4 with the locking pin shown in a second position.
Figure 10:
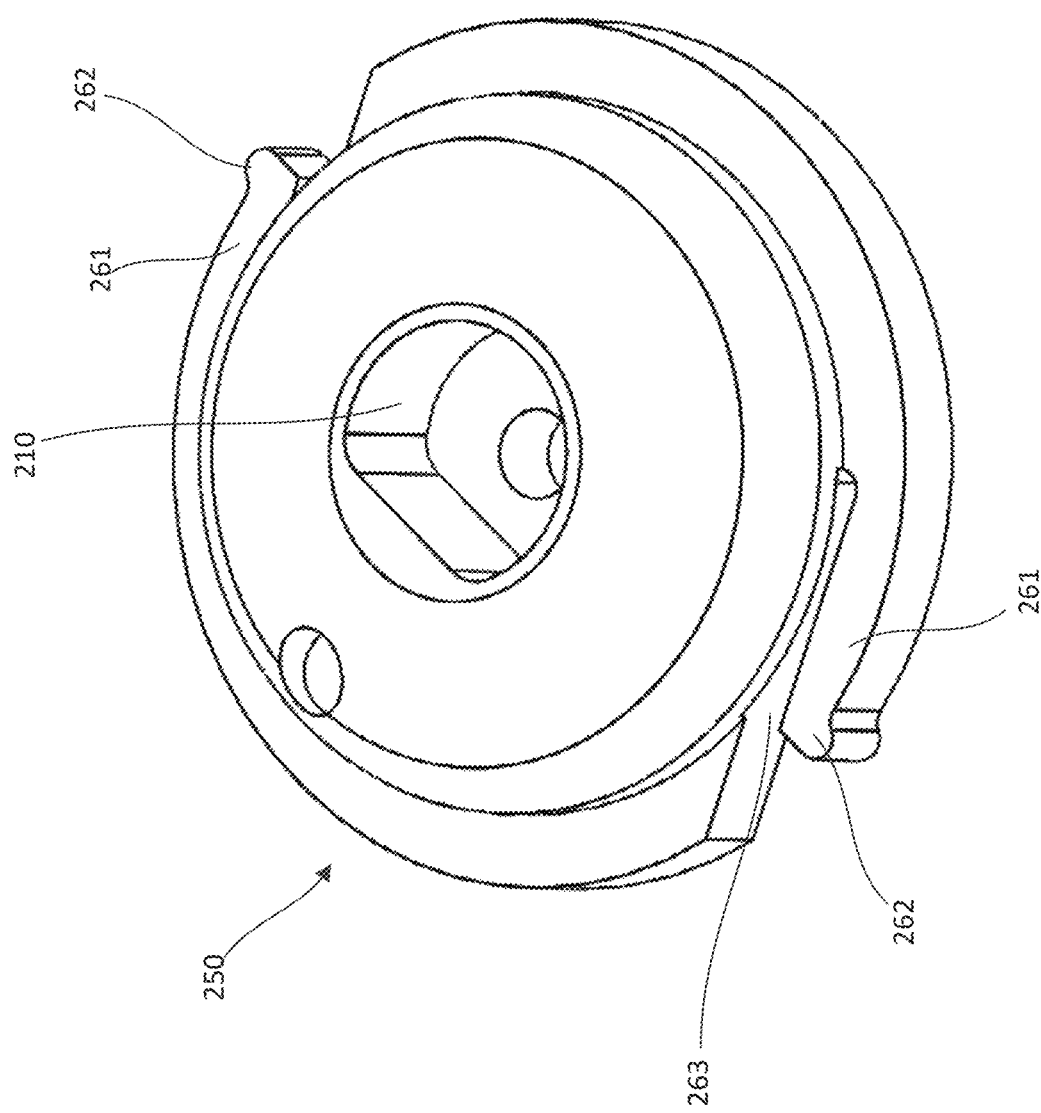
FIGS. 10 and 11 are a top perspective and a bottom perspective view, respectively, of a hub member of the epicardial anchor device of FIG. 4.
Figure 11:
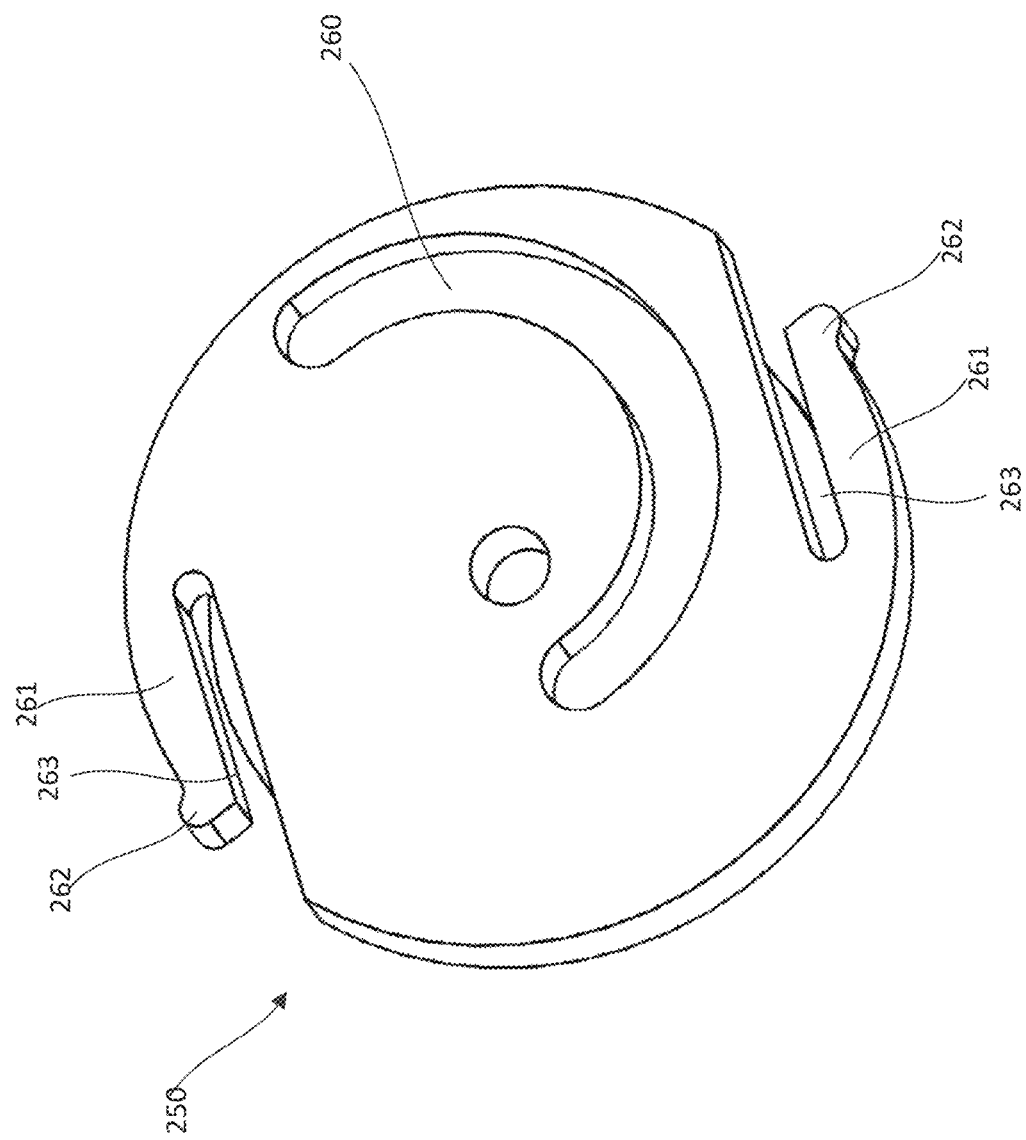
Figure 12:
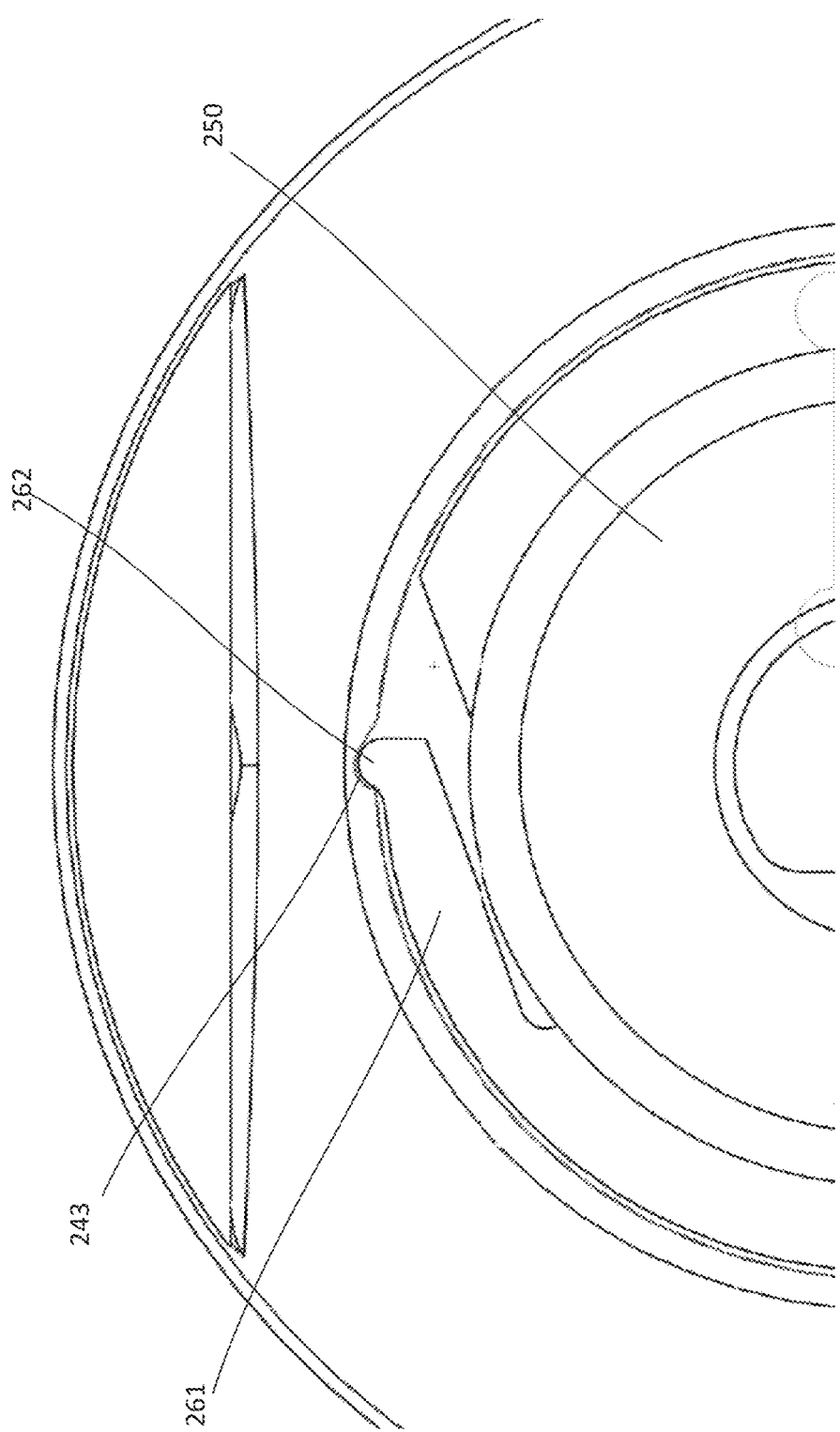
FIG. 12 is an enlarged top view of a portion of the epicardial anchor device of FIG. 4.

An outer perimeter portion of the hub 250 is received within the retaining channel 251 such that the hub 250 can rotate relative to the base member 240 to actuate the locking pin assembly 226 as described in more detail below. As shown, for example, in FIGS. 10 and 11, the hub 250 includes arms 261 with protrusions 262. The protrusions 262 can be received within cutouts 243 of the base member 240 and act as a stop or limit to the rotation of the hub 250. The hub 250 defines slots 263 that enable the arms 261 to flex and allow the protrusions 262 to be moved in and out of the cutouts 243. As shown, for example, in FIGS. 9 and 10 the hub 950 defines a curved channel 250 on a bottom portion of the hub 950. The curved channel 250 is asymmetrical (or spiral) and receives the driver portion 246 of the locking pin assembly 226. As the hub 250 is rotated relative to the base member 240, the hub 250 acts as a cam to move the locking pin assembly 226 linearly within the locking pin channel 234. The locking pin assembly 226 can be moved from a first position in which the piercing portion 249 is disposed outside of the tether passageway 235 as shown in FIGS. 7 and 8, and a second position in which the piercing portion 249 extends through the tether passageway 235 as shown in FIG. 9. The pin member 253 (see, e.g., FIG. 8) can be formed with a metal material that is more radio-opaque than the other components of the anchor device and thus visible to the user (e.g. physician) using conventional imaging modalities to enable the user to confirm that the locking pin assembly 226 has been fully moved to the second position.

In use, when the locking pin assembly 226 is in the first position, a tether (not shown) coupled to, for example, a prosthetic mitral valve and extending through a puncture site in the ventricular wall of a heart can be inserted through the tether passageway 235. The hub 250 can then be rotated 180 degrees to move the locking pin assembly 226 linearly within the locking pin channel 234 such that the piercing portion 249 extends through the tether passageway 235 and engages or pierces the tether, securing the tether to the tether attachment member 224. For example, the hub 250 also defines a driver receiving opening 210 configured to receive a mating portion of a positioning device (described below, e.g., with reference to positioning devices 242, 342 and 442). The positioning device can be used to rotate the hub and actuate the locking pin assembly 226. When the locking pin is in the first position, the protrusions 262 of the hub 250 are each disposed within one of the cutouts 243 of the base member 240 (i.e., a first protrusion is in a first cutout, and a second protrusion is in a second cutout). The hub 250 can then be rotated 180 degrees such that the protrusions 262 are moved out of the cutouts 243 of the base member 240 and at the end of the 180 degrees the protrusions 262 are moved into the other of the cutouts 243 of the base member 240 (i.e., the first protrusion is now in the second cutout, the second protrusion is now in the first cutout).

The base member 240 can also include cutout sections 266 and define side openings 267 (see, e.g., FIGS. 4 and 5) that can be used to couple a positioning device to the epicardial anchor device 200. For example, FIGS. 13-17B illustrate a positioning device 242 that can be used to deploy and position an epicardial anchor device such as anchor device 200.

Figure 13:
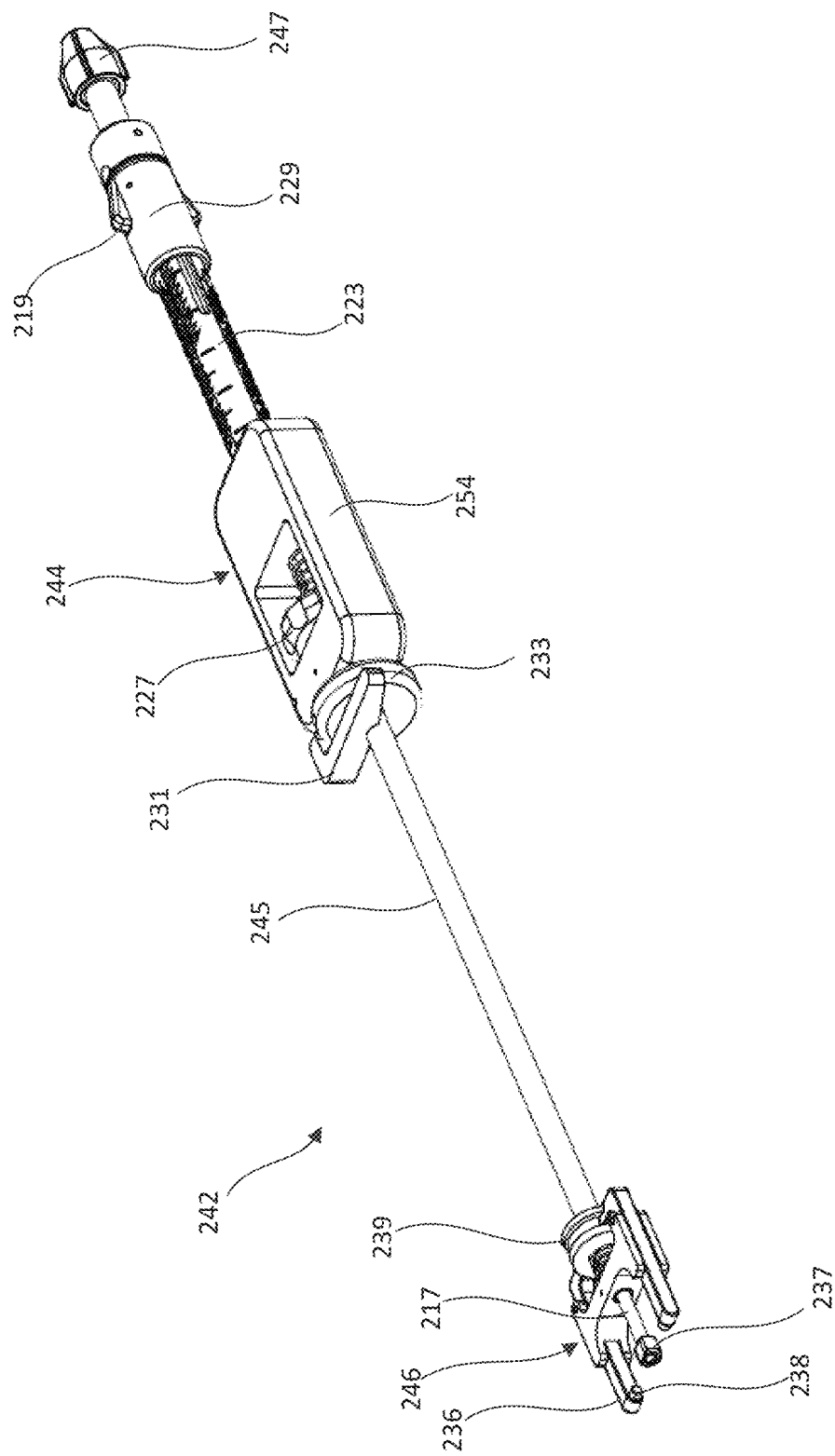
FIG. 13 is a perspective view of a positioning device, according to an embodiment.
Figure 14:
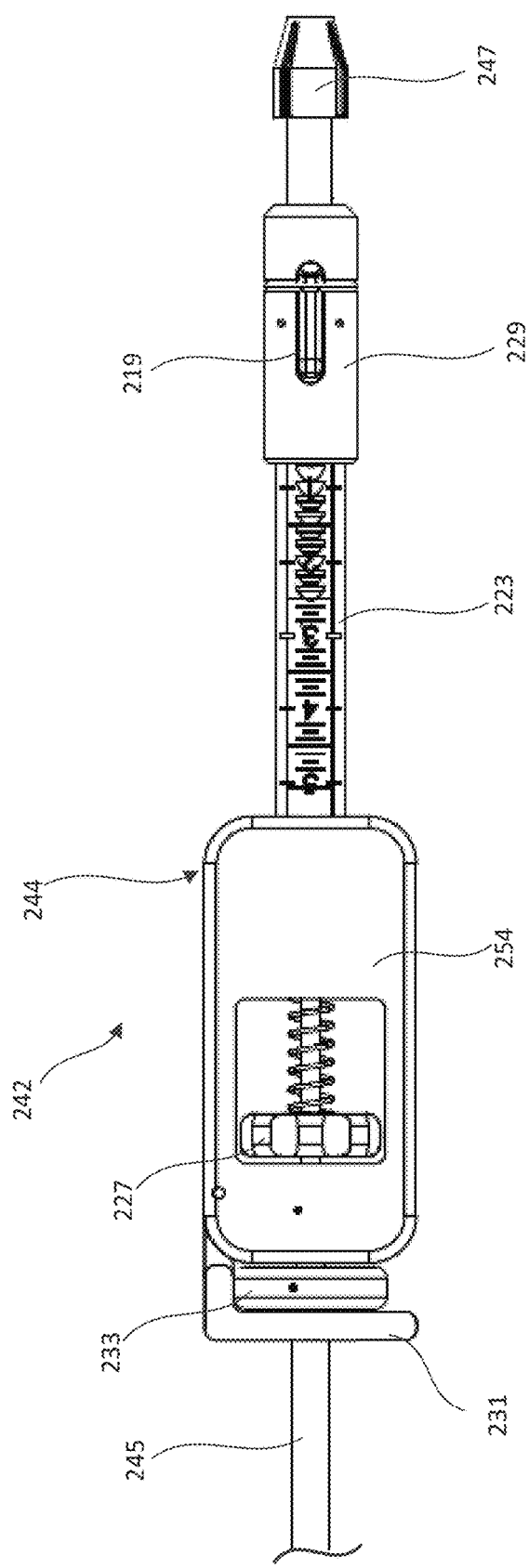
FIG. 14 is a top view of a portion of the positioning device of FIG. 13.

As shown in FIG. 13, in this embodiment, the positioning device 242 includes an elongate member 245, a docking member 246 coupled to a distal end of the elongate member 245, a handle assembly 244 and a tether securing member 247. The handle assembly 244 includes a housing 254, a transparent tube segment 223 with indications disposed thereon, a tension member 229, a thumb dial 227, a release button 233 and a safety lever 231.

Figure 15:
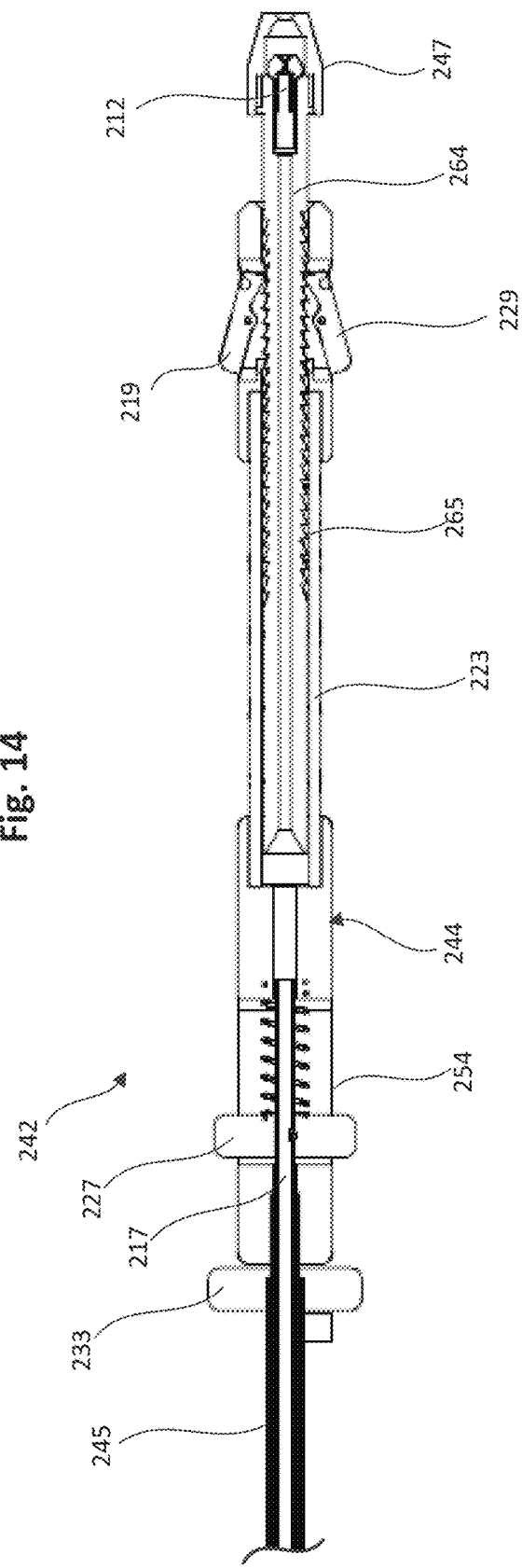
FIG. 15 is a cross-sectional view of the portion of the positioning device of FIG. 14.

The handle assembly 245 is coupled to the tether securing device 247 with a rod member 264 (see, e.g., FIG. 15). The handle assembly 245 is also coupled to the elongate member 245, which is coupled to the docking member 246. The docking member 246 includes coupling arms 236 with coupling pins 238 extending inwardly from the coupling arms 236. The coupling pins 238 are configured to be received within the side openings 267 of the anchor device 200 described above, and the coupling arms 236 can engage the cutout sections 266 of the anchor device 200. The coupling arms 236 have hinged joints which are coupled to a disc member 239. The disc member 239 can be coupled to or incorporated with or monolithically formed with the elongate member 245. A spring 216 disposed between the disc member 239 and the arms 236 biases the coupling arms 236 in a closed position as shown, for example, in FIGS. 13, 15 and 16. The coupling arms 236 can be moved to an open position (not shown) to allow for the anchor device 200 to be received between the coupling arms 236 to couple and release the anchor device 200 to and from the positioning device 242. Actuation of the docking member 246 is described in more detail below. An inner driver member 217 is movably disposed within a lumen defined by the elongate member 245 and extends through the docking member 246. The inner driver member 217 includes a shaped distal tip 237 that is configured to be matingly received within the driver receiving opening 210 of the anchor device 200. The inner driver member 217 is operatively coupled to the thumb dial 227 of the positioning device 242 and can be used to actuate the locking pin assembly 226 of the anchor device 200 to secure a tether to the anchor device 200, as described below.

The safety lever 231 is hingedly coupled to the housing 254 and can be moved from a first position as shown, for example, in FIG. 13, in which the safety lever 231 prevents the release button 233 from moving and a second position (not shown) in which the safety lever 231 is pivoted or moved in a direction upward away from the elongate member 245 such that the release button 223 can be moved as desired as described in more detail below.

In use, a tether (not shown) extending from a prosthetic mitral valve and outside of the heart can be inserted through the epicardial anchor device 200 and threaded through a lumen of the inner driver member 217, through the handle assembly 244, and out through the tether securing device 247.

To releasably couple and uncouple the anchor device 200 to and from the positioning device 242, the safety lever 231 is moved to its second position in which the release button 233 is free to move. The release button 233 is fixedly coupled to the elongate member 245 such that as the release button is moved distally, the elongate member 245 moves distally, and in turn the disc member 239 moves distally compressing the spring 216 and actuating the hinged coupling arms 236 of the docking member 246 to open wide enough such that the anchor device 200 can be place therebetween. The distal tip 237 of the driver member 217 is received within the opening 210 of the anchor device 200. The release button 233 can then be moved proximally to allow the coupling arms 236 to move back to their biased closed position (e.g., closer together) and be inserted into the side openings 267 of the anchor device 200. The safety lever 231 can then be moved back to its first position, as shown in FIG. 13.

With the anchor device 200 coupled to the positioning device 242, the anchor device 200 can be positioned at a desired location on the outer surface of the ventricular wall of the heart, such as for example, at the apex. The tether extending through the positioning device 242 and out the proximal end of the positioning device 242 can be pulled proximally to a desired tension. When the tether is drawn/pulled to the desired tension, e.g., such that the deployed prosthetic valve seats firmly in the native annulus and any regurgitation seen on fluoroscopy or echocardiography is no longer present, the practitioner can fine tune the tensioning by visually observing the tether within the transparent tube segment 223 and compare the longitudinal distance travelled against an implant position scale. When the tether is suitably located, the locking pin assembly 226 of the anchor device 200 can be actuated by the positioning device 242 to lock the tether in place on the epicardial anchor device 200. For example, the thumb dial 227, which is operatively coupled to the driver member 217, can be rotated to actuate the locking pin assembly 226 of the anchor device 200 to pierce the tether and secure the tether to the anchor device 200.

Figure 17A:
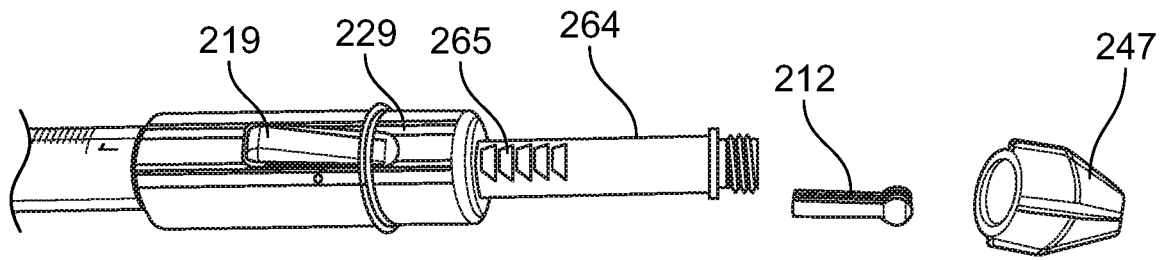
FIG. 17A is a perspective view of a portion of the positioning device of FIG. 13 shown partially exploded.
Figure 17B:
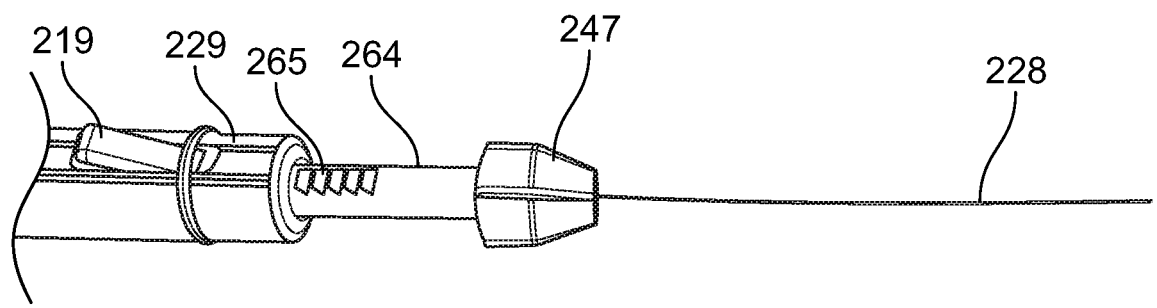
FIG. 17B is a perspective view of the portion of the positioning device of FIG. 17A.
Figure 20:
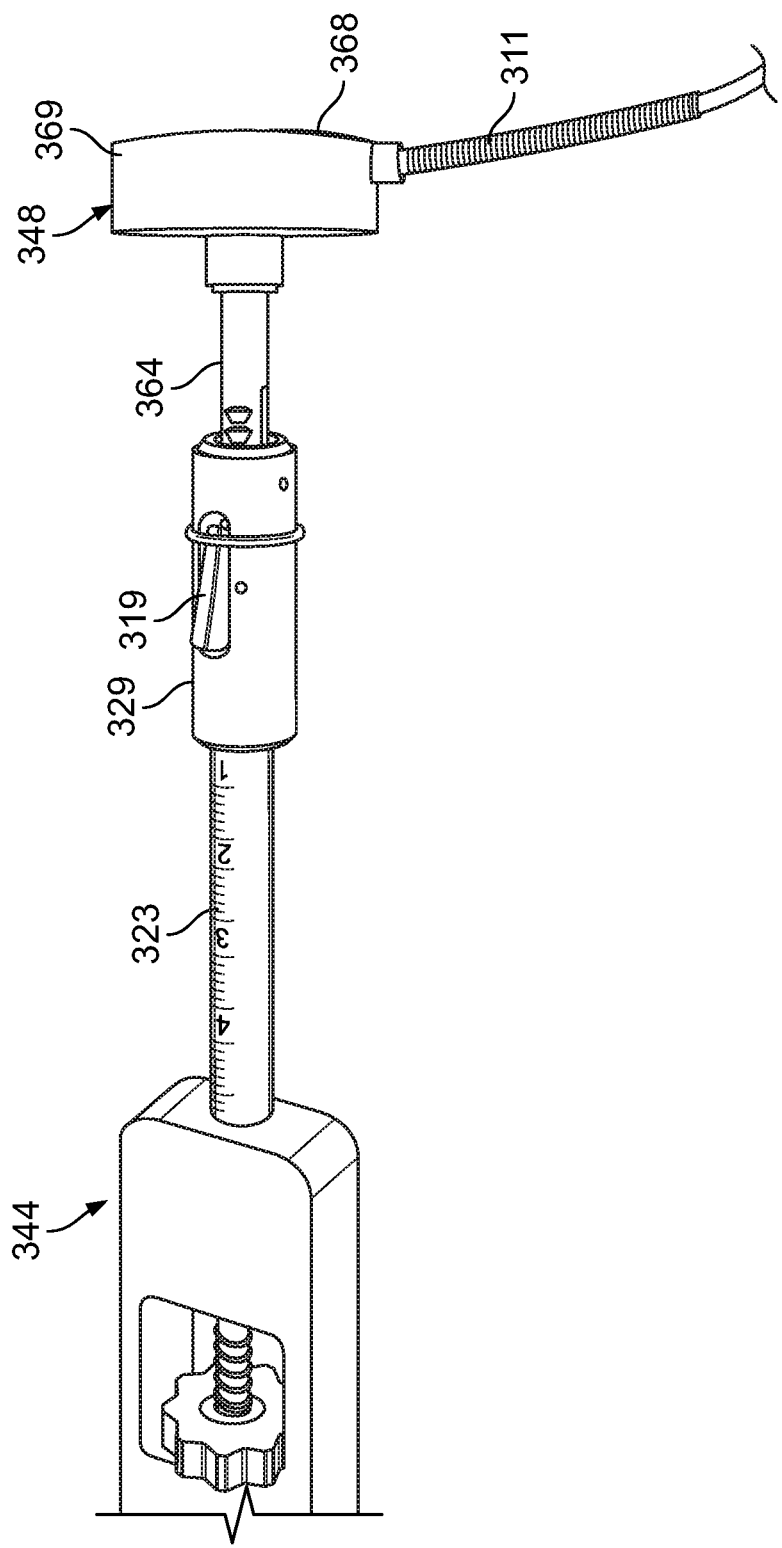
FIG. 20 is a perspective view of the portion of the positioning device of FIG. 19.
Figure 21:
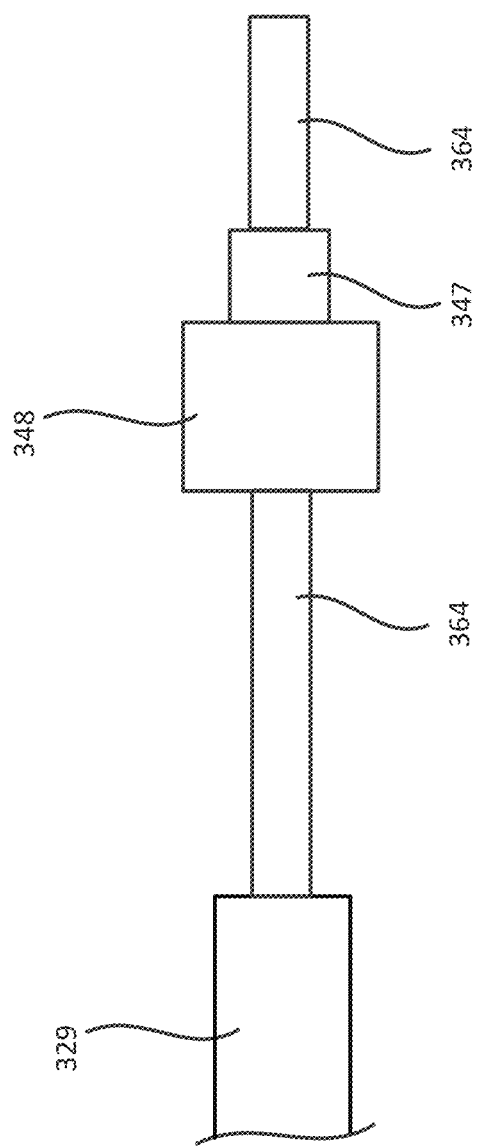
FIG. 21 is a schematic illustration of a portion of the positioning device of FIG. 18.

Prior to pinning the tether to the anchor device 200, it may be desirable to make small adjustments or fine tuning to the position of the anchor device 200 and/or to the tension of the tether. To make such adjustments or fine tuning, the tether securing device 247 can be used to secure the tether at a fixed position on the positioning device 242, such that the anchor device 200 can be pushed distally snug to the outer wall of the heart. For example, in this embodiment, the tether securing device 247 includes a collet 212 (see, e.g., FIGS. 15 and 17A) that provides a friction fit against the tether when the tether securing device 247 is rotated. If an adjustment to the tension of the tether and/or to the position of the anchor device 200 is desired, with the tether securing device 247 holding the tether in a fixed position, the tension member 229 can be actuated to allow the handle assembly 244, elongate member 245 and docking member 246 to be moved distally relative to the rod member 264 to which the tether securing device 247 is coupled. For example, as shown in FIGS. 17A and 17B, grooved teeth 265 of the rod member 264 allow the handle assembly 244 to be incrementally moved distally. Alternatively, the push buttons 219 on the tension member 229 can be depressed which will release the grooved teeth 265 and allow the handle assembly 244 to be slid freely relative to the rod member 264.

When the anchor device and tether have been secured in a desired position and at a desired tension, the positioning device 242 can be actuated to pin the tether to the anchor device 200 as described above, and then the epicardial anchor device 200 can be released from the positioning device 242. The portion of the tether extending from the anchor device 200 can be cut to a desired length and/or tied off.

FIGS. 18-21 illustrate another embodiment of a positioning device that can be used to position an epicardial anchor device such as anchor device 200. As with the previous embodiment, the positioning device 342 includes an elongate member 345, a docking member 346 coupled to a distal end of the elongate member 345, and a handle assembly 344 coupled to the elongate member 345. The handle assembly 344 includes a housing 354, a transparent tube member 323 with indications disposed thereon, a tension member 329, a thumb dial 327, a release button 333 and a safety lever 331. Each of these components can be the same as or similar to the corresponding components of positioning device 242 and are therefore not discussed in detail with respect to this embodiment.

In this embodiment, the positioning device 342 also includes a force sensor device 348 coupled at a proximal end of the positioning device 342. The force sensor device 348 can be coupled to the housing 344 via a rod member 364 similar to the rod member 264. The force sensor device 348 includes a sensor housing 369 defining an interior region that receives a load cell 368. In some embodiments, the load cell can include, for example a piezoelectric sensor. In some embodiments the load cell 368 can include miniature strain gauges. The load cell 368 can be electrically coupled to a transducer (not shown) or a data acquisition module (not shown) via a cable 311, which in turn can communicate with an electronic device (not shown) configured to display the output of the force sensor device 348 as described above with respect to FIG. 3. The electronic device can be, for example, a monitor or display of a computer, such as a laptop computer or a desktop computer, or a handheld electronic device such as a tablet, phone or other electronic device configured to receive and display the results of the force sensor device 348.

The positioning device 342 can also include a tether securing device 347 coupled proximally to force sensor device 348. The tether securing device 347 includes a collet (not shown) that provides a friction fit against a tether when the tether securing device 347 is rotated as described for the previous embodiment. As shown in the schematic illustration of FIG. 21, the rod member 364 can extend through the force sensor device 348 and the tether securing device 347 can be coupled thereto.

In use, as with the previous embodiment, a tether (not shown) extending from a prosthetic mitral valve and outside of the heart can be inserted through an epicardial anchor device, threaded through the elongate member 345, through the handle assembly 344, and out through the tether securing device 347. The anchor device can be releasably coupled to the positioning device 342 in the same manner as described above for positioning device 242 and the locking pin assembly of the anchor device can be actuated to pin the tether to the anchor device as described above.

The anchor device 200 can be positioned at a desired location on the outer surface of the ventricular wall of the heart, such as for example, at the apex. The tether extending through the positioning device 342 can be pulled proximally to a desired tension. In this embodiment, the tension on the tether can be measured and displayed for the practitioner. For example, tether securing device 347 exerts a compressive force on the load cell 368 as the tether is being pulled through. The compressive force displaces the load cell, which causes a deflection of the load cell which is detected by the sensor(s) within the load cell 368. The deflection data is sent to the data acquisition module which in turn provides pressure data to be viewed on an electronic display. When the desired tension on the tether is achieved, the tether securing device 347 can be used to secure the tether at a fixed position relative to the positioning device 342 as described above.

If an adjustment to the tension of the tether and/or to the position of the anchor device on the tether is desired, with the tether securing device 347 holding the tether in a fixed position, and while holding the tether securing device 347, the tension member 329 can be actuated to allow the handle assembly 344, elongate member 345 and docking member 346 to be moved distally relative to the rod member 364 and tether securing device 347. For example, as previously described, the tension member 329 can be used to incrementally move the handle assembly 344 distally or push buttons 319 on the tension member 329 can be depressed which will release grooved teeth 365 on the rod member 364 and allow the handle assembly 344 to be slid freely relative to the rod member 364.

When the anchor device and tether have been secured in a desired position and at a desired tension, the positioning device 442 can be actuated to release the epicardial anchor device. The portion of the tether extending from the anchor device can be cut to a desired length and/or tied off.

FIGS. 22-28 illustrate a positioning device 442 according to another embodiment. The positioning device 442 can be configured the same as or similar to and provide the same or similar functions as the above described embodiments. The positioning device 442 includes a docking member 446 coupled to a distal end of an elongate member 445, a handle assembly 444 and a force sensor device 448. The positioning device 442 can also include a tether securing device (not shown) that can be the same as or similar to the tether securing devices described above. The handle assembly 444 includes a housing 454 having a transparent segment 423 with indications disposed thereon, a tension member 429, a switch 427, a release knob 433 and a safety lever 431.

The handle assembly 445 is coupled to the elongate member 445, which is coupled to the docking member 446. The docking member 446 includes coupling arms 436 with coupling pins 438 extending inwardly from the coupling arms 436. As with the previous embodiments, the coupling pins 438 are configured to be received within the side openings of an anchor device such as anchor device 200 described above. The coupling arms 436 can also engage the cutout sections of the anchor device as described above. The coupling arms 436 have hinged joints which are coupled to a disc member 439 which is coupled to or incorporated or monolithically formed with the elongate member 445. A spring 416 is disposed between the disc member 439 and the arms 436 and biases the arms 436 in a closed position as shown, for example, in FIGS. 13, 15 and 16. The coupling arms 436 can be moved to an open position (not shown) to allow for the anchor device to be received between the coupling arms 436 to couple and release the anchor device to and from the positioning device 442. Actuation of the docking member 436 is described in more detail below. An inner driver member 417 is movably disposed within a lumen defined by the elongate member 445 and extends through the docking member 446. The inner driver member 417 includes a shaped distal tip 437 that is configured to be matingly received within a driver receiving opening of the anchor device as described above. The inner driver member 417 is operatively coupled to the switch 427 of the positioning device 442 and can be used to actuate the locking pin assembly of the anchor device to secure a tether to the anchor device, as described above for previous embodiments.

Figure 22:
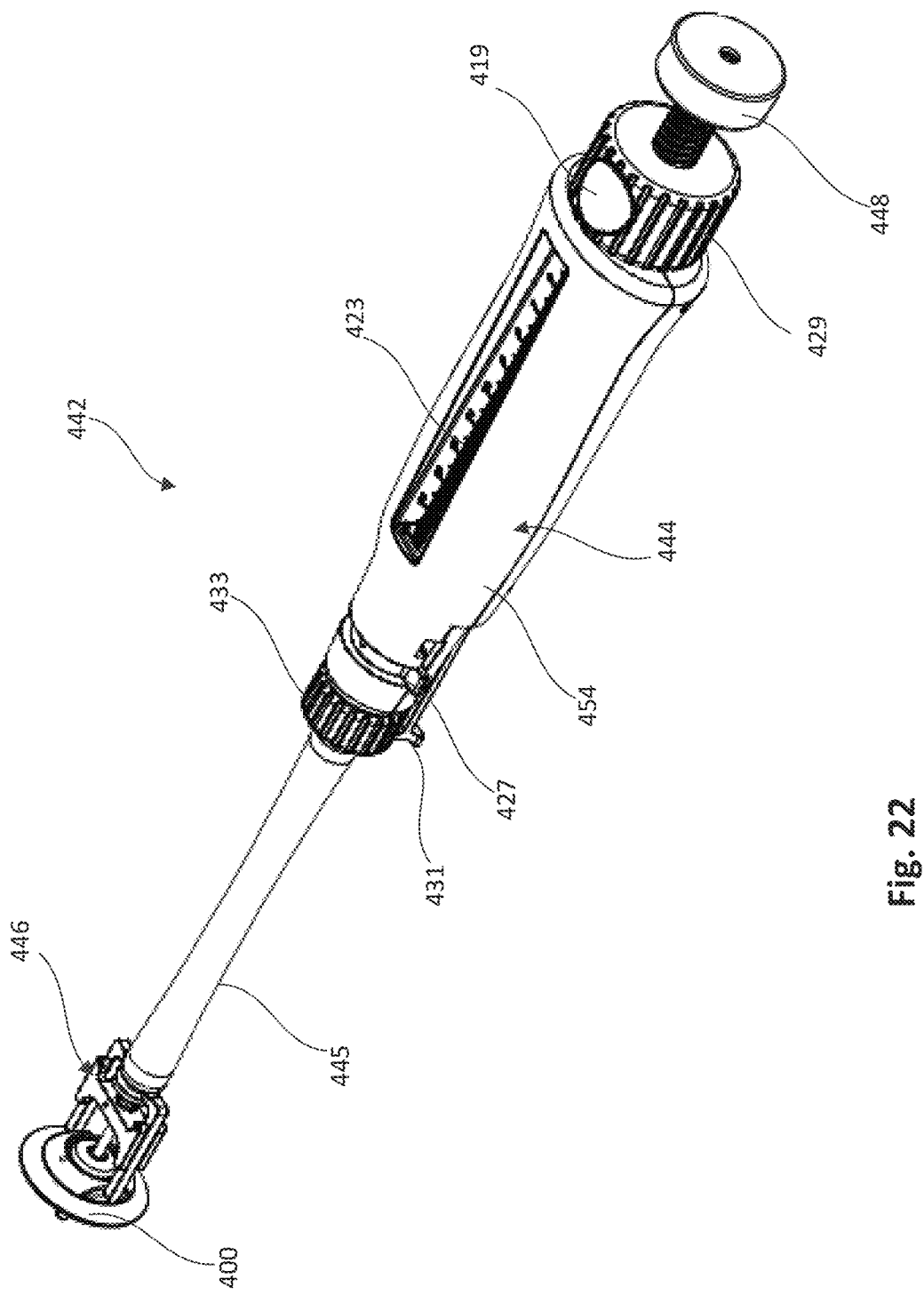
FIG. 22 is a perspective view of a positioning device, according to another embodiment, shown coupled to an epicardial anchor device.
Figure 23:
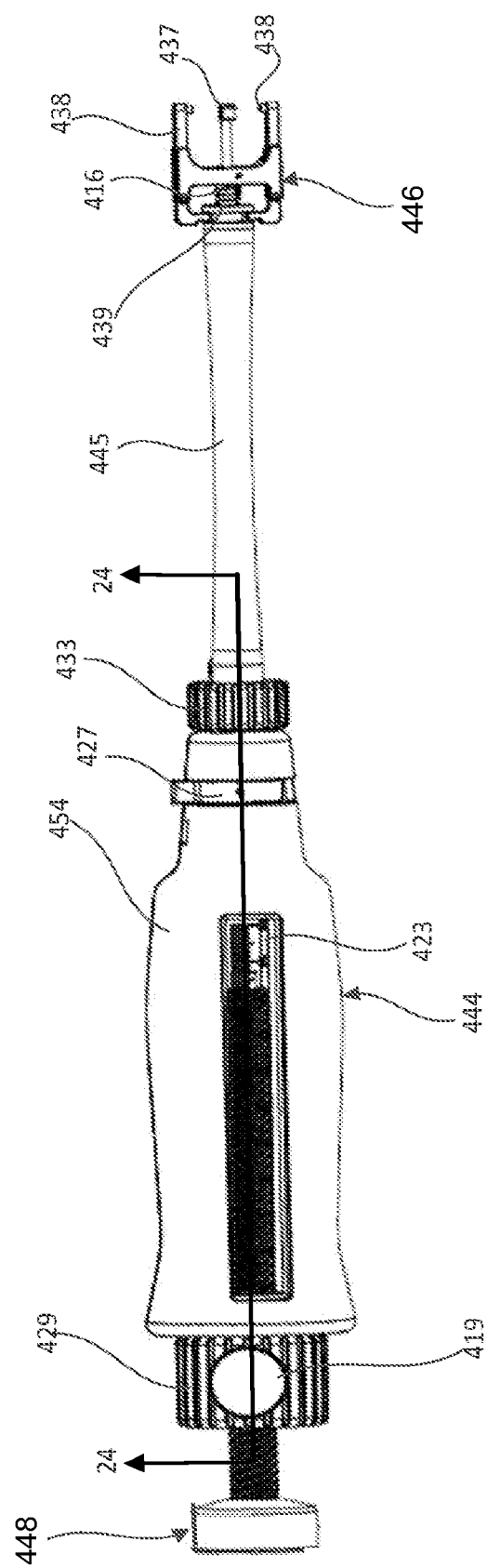
FIG. 23 is a top view of the positioning device of FIG. 22.
Figure 24:
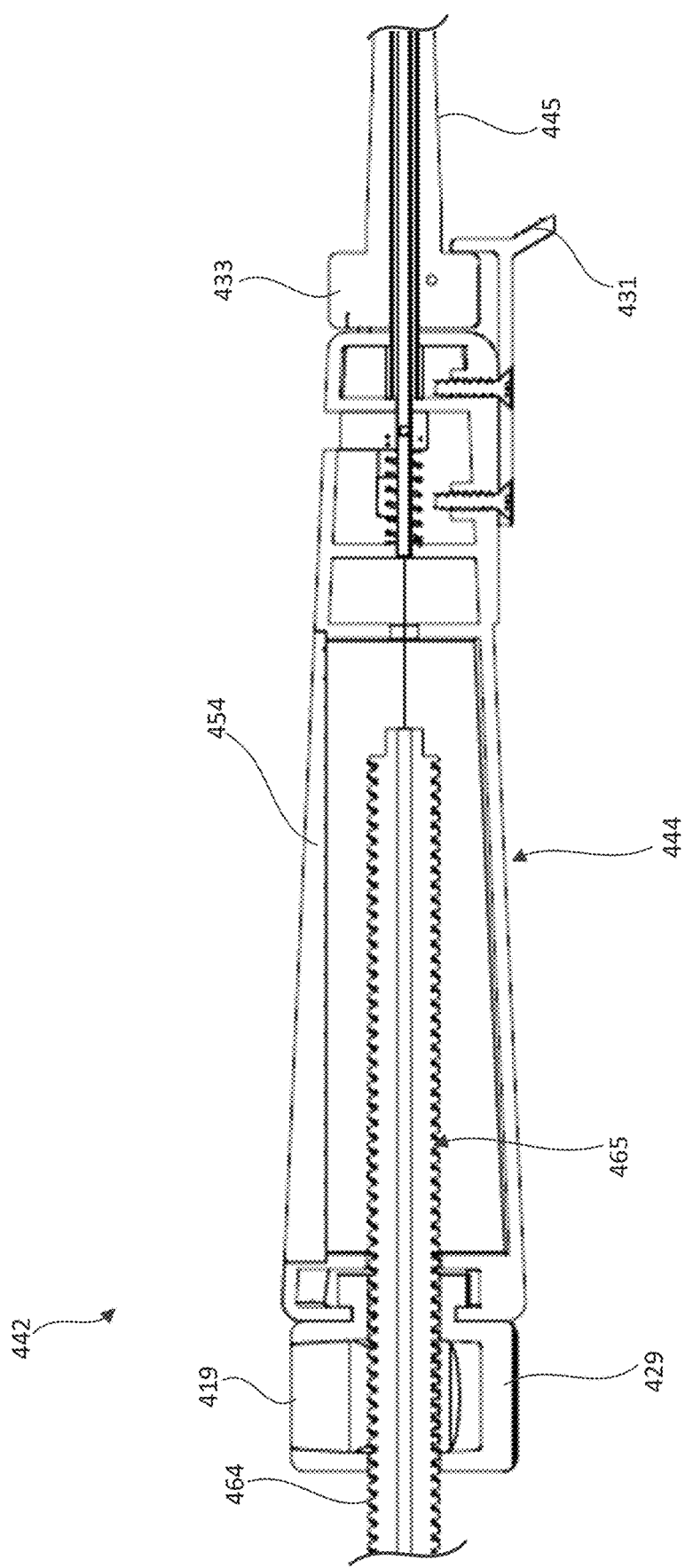
FIG. 24 is a cross-sectional view of a portion of the positioning device of FIG. 22, taken along line 24-24 in FIG. 23.
Figure 25:
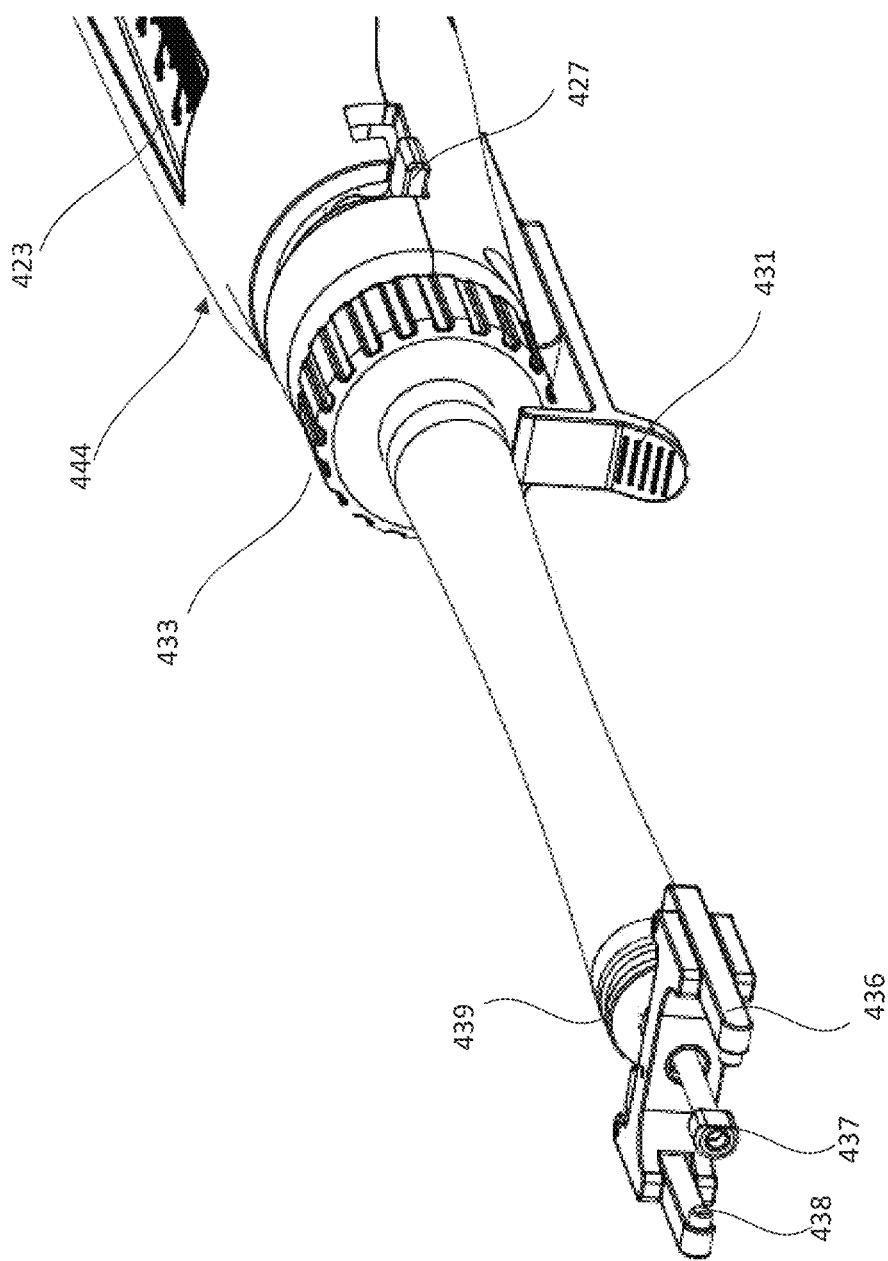
FIG. 25 is a perspective view of a portion of the positioning device of FIG. 22.
Figure 27:
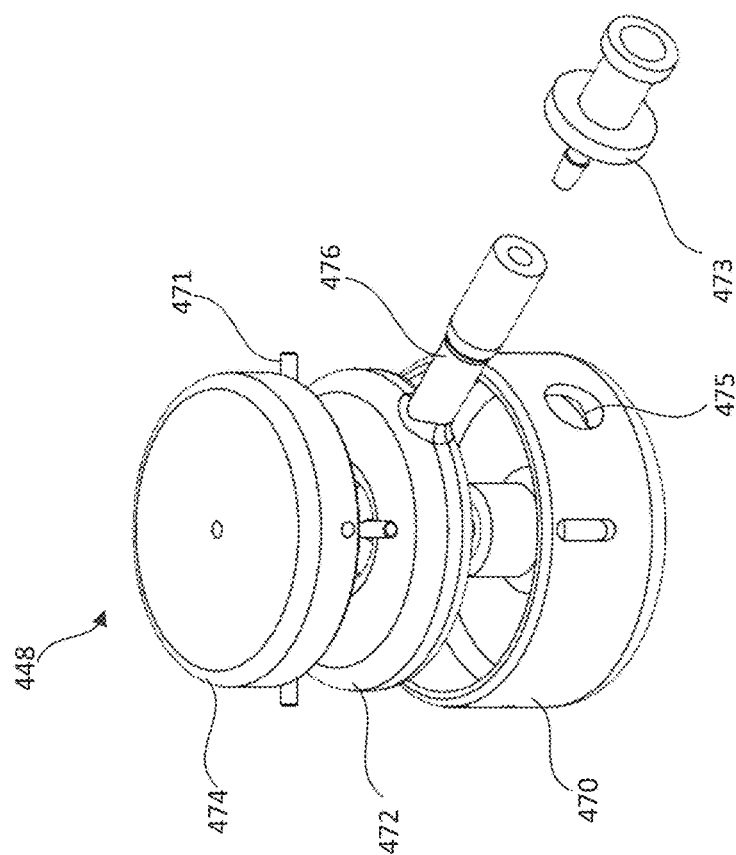
FIG. 27 is an exploded perspective view of the force sensor device of FIG. 26.
Figure 26:
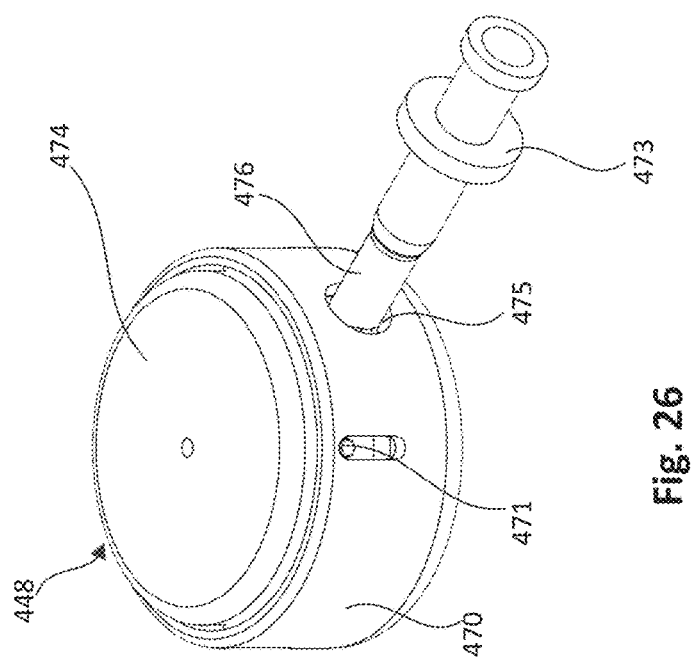
FIG. 26 is a perspective view of a force sensor device of the positioning device of FIG. 22.

The safety lever 431 can be moved from a first position as shown in FIGS. 22, 24 and 25 in which the safety lever 431 prevents the release knob 433 from moving and a second position (not shown) in which the safety lever 431 is moved in a direction downward away from the elongate member 445 such that the release knob 433 can be moved as desired as described in more detail below.

As shown in FIGS. 26-30, in this embodiment, the force sensor device 448 includes a sensor housing 470, a fluid chamber 472 and a load washer 474. The fluid chamber 472 defines an interior region that can contain a fluid and that is in fluid communication with a conduit 476. The fluid chamber 472 is received within the sensor housing 470 and the conduit 476 extends out of the sensor housing 470 through an opening 475 defined by the sensor housing 470. The load washer 474 is disposed over the fluid chamber 472 and is coupled to the sensor housing 470 with pins 471 such that the load washer 474 can move within slots 477 defined by the sensor housing 470. This allows for the fluid chamber 472 to reduce and expand in size within the interior region defined collectively by the sensor housing 470 and the load washer 474. A fluid port connector 473 is coupled to the conduit 476. The fluid port connector 473 can be for example, a Luer connector. The fluid port connector 473 can be coupled to a pressure transducer (not shown) which in turn can be coupled to a device that can be used to display pressure readings received from the pressure transducer. In some embodiments, the pressure transducer can be incorporated within the force sensor device 448, or coupled directly to or proximate to the force sensor device 448. During use, force is exerted on the load washer 474 which in turn exerts a compressive force on the fluid chamber 472 causing the pressure of the fluid in the interior region of the fluid chamber 472 to be increased. This increased pressure can be communicated through the fluid from the fluid chamber 472 to and through the conduit 476. The force sensor device 448 can be used to measure the load on a tether extending through the positioning device 442. For example, the positioning device 442 can include a tether securing member (not shown) that can be configured the same as or similar to the tether securing device 247 described above. In a similar manner as shown for force sensor device 448 (see, e.g., FIG. 21), the rod member 464 can extend through the force sensor device 448 and the tether securing device can be coupled to the rod member 465 and disposed on a proximal side of the force sensor device 448 in contact with the load washer 474. As the tether is pulled through to a desired tension, the tether securing device exerts a force on the load washer 474.

In use, a tether (not shown) extending from a prosthetic mitral valve and outside of the heart can be inserted through an epicardial anchor device 400 (see, FIG. 22) and threaded through a lumen of the inner driver member 417, through the handle assembly 444, and out through the tether securing device (not shown). For purposes of the following description, the epicardial anchor device 400 can be the same as the epicardial anchor device 200 described above.

To releasably couple and uncouple the anchor device 400 to and from the positioning device 442, the safety lever 431 is moved to its second position in which the release knob 433 is free to move. The release knob 433 is fixedly coupled to the elongate member 445 such that as the release knob 433 is moved distally, the elongate member 445 moves distally, and in turn the disc member 439 moves distally compressing the spring 416 and actuating the hinged coupling arms 436 of the docking member 446 to open wide enough such that the anchor device 400 can be place therebetween. The distal tip 437 of the driver member 417 is received within the mating opening of the anchor device 400 as described above for anchor device 200. The release knob 433 can then be moved proximally to allow the coupling arms 436 to move back to their biased closed position (e.g., closer together) and be inserted into the side openings of the anchor device 400. The safety lever 431 can then be moved back to its first position, as shown in FIGS. 24 and 25.

Figure 29:
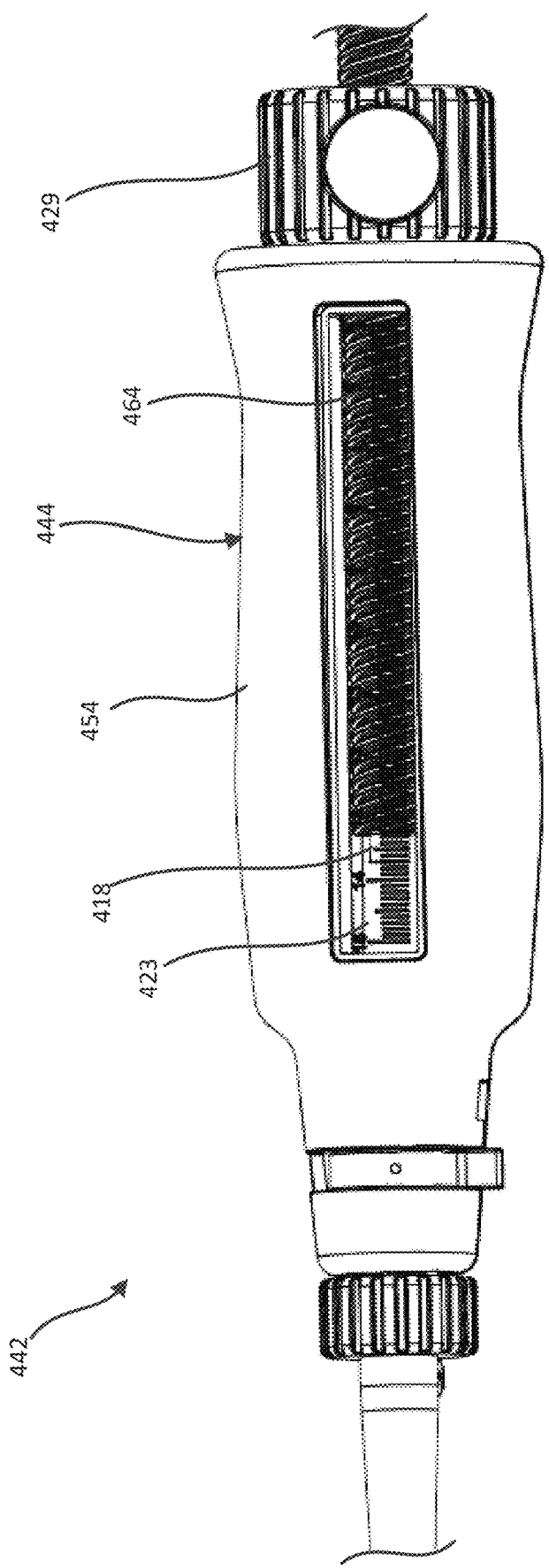
FIG. 29 is a perspective view of a portion of the positioning device of FIG. 22.
Figure 32:
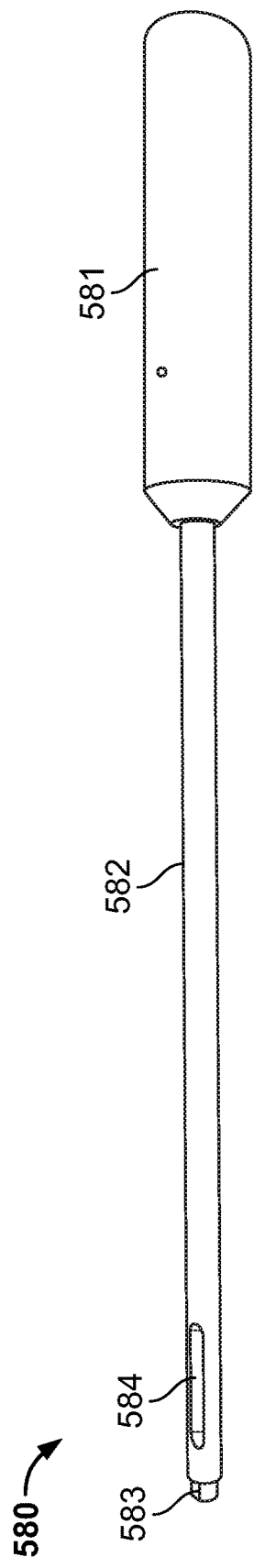
FIG. 32 is a top view of a tether release tool, according to an embodiment.
Figure 39:
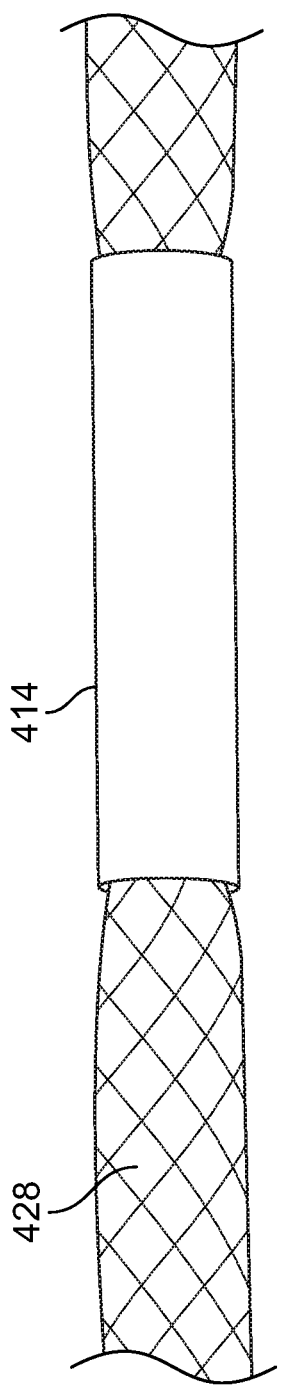
FIG. 39 is a side view of a portion of a tether with a marker band according to an embodiment.

With the anchor device 400 coupled to the positioning device 442, the anchor device 400 can be positioned at a desired location on the outer surface of the ventricular wall of the heart, such as for example, at the apex. The tether extending through the positioning device 442 and out the proximal end of the positioning device 442 can be pulled proximally to a desired tension. When the tether is drawn/pulled to the desired tension, e.g., such that the deployed prosthetic valve seats firmly in the native annulus and any regurgitation seen on fluoroscopy or echocardiography is no longer present, the practitioner can fine tune the tensioning by visually observing the tether within the transparent segment 423 and comparing the longitudinal distance travelled against an implant position scale. Further, as shown in FIG. 29, the transparent segment 423 includes markings or indications 415. In this example, the markings 415 include indications between 5 and 15 centimeters. Different indications and/or increments can be used as appropriate. A distal portion of the rod member 464 can be viewed through the transparent segment 423 and includes an indicator 418 at a distal end of the rod member 464. The indicator 418 can be a marking on the rod member 464 or a separate component coupled to the rod member 464. In some embodiments, the indicator 418 can be color coded. The indicator 418 shows the location of the rod member 464 as the rod member 464 is moved in a proximal and distal direction and corresponds to a distance between the bottom surface of the epicardial pad device 400 that contacts the heart and the annulus of the heart valve. For example, the markings 415 can be used to identify the location of the indicator 418 on the distal end of the rod member 464. The distance between the bottom surface of the epicardial pad device 400 that contacts the heart and annulus of the heart can be determined based on a known length of the tether. For example, a proximal end portion of the tether extending out of the positioning device 442 can have a marker 414 (see FIG. 39 illustrating a tether 428 with a marker 414 coupled thereto). The marker 414 can be for example, a stainless steel hypotube or band crimped or swaged onto the tether. The marker 414 on the tether can indicate a preset distance from where the prosthetic mitral valve is seated in the annulus. For example, the marker 414 can be a set distance of 40 mm from where the tether is attached at the cuff of the prosthetic mitral valve. From this, when the tether is extended through the positioning device 442, depending on the tension applied to the tether, the location of the indicator 418 on the rod member 464 can represent the distance between the epicardial pad device 400 that contacts the heart and annulus of the heart.

When the tether is suitably located, the locking pin assembly of the anchor device 400 can be actuated by the positioning device 442 to lock the tether in place on the epicardial anchor device 400. For example, the switch 427, which is operatively coupled to the driver member 417, can be actuated to rotate the driver member 417 and actuate the locking pin assembly of the anchor device 400 to pierce the tether and secure the tether to the anchor device 400. In some embodiments, the switch 427 can be moved or flipped 180 degrees. For example, the driver member 417 can be moved 180 degrees to rotate the driver inward to actuate the pin locking assembly of the anchor device 400 and secure the tether, and then back 180 degrees to move the driver member 417 in the opposite direction to release the tether.

Prior to pinning the tether to the anchor device 400, it may be desirable to make small adjustments or fine tuning to the position of the anchor device 400 and/or to the tension of the tether. To make such adjustments or fine tuning, the tether securing device (not shown) can be used to secure the tether at a fixed position on the positioning device 442, such that the anchor device 400 can be pushed distally snug to the outer wall of the heart in a similar manner as described above with respect to positioning device 242. For example, in this embodiment, the rod member 464 can move proximally and distally relative to the handle assembly 444. While holding the tether securing device, the tension member 429 can be actuated (e.g., rotated) such that the rod member 464 rotates proximally with the tether securing device (not shown). For example, the tension member 429 can be coupled to the rod member 464 such that rotating of the tension member 429 causes the rod member to move proximally or distally depending on the direction of rotation of the tension member 429. This can provide the ability to make fine adjustments to the tension on the tether. In addition, the release button(s) 419 on the tension member 429 can be pressed to allow the tension member 429 to disengage from the teeth 465 of the rod member 464 and be freely slid relative to the rod member 464. In this manner, the tension member 429 can be slid distally, which in turn moves the handle assembly 444, elongate member 445 and docking member 446 distally relative to the rod member 464 and tether securing device.

As with the previous embodiment, the tension on the tether can be measured and displayed for the practitioner via the force sensor device 448. For example, as described above, the tether securing device (not shown) can exert a compressive force on the load washer 474 as the tether is being pulled through.

When the anchor device and tether have been secured in a desired position and at a desired tension, the positioning device 442 can be actuated to pin the tether to the anchor device 400 as described above, and then the epicardial anchor device 400 can be released from the positioning device 442. The portion of the tether extending from the anchor device 400 can be cut to a desired length and/or tied off.

FIG. 31 illustrates a tension limiting device (also referred to as "tensioner") that can be included in the positioning devices described herein. The tensioner 480 can be incorporated within, for example, the tension member 429' and can be used to limit the amount of load (e.g. tension T) that can be set during prosthetic valve implantation. The tensioner 477 includes ratchet members 478 and 479 that skip over each other when maximum tension on the lead screw is achieved. A spring 483 is coupled to the rod member 464 and applies tension on the ratchet members 478 and 479. The ratchet member 479 can be coupled to the housing of the tension member 429 and can move axially along the rod member 464. The ratchet member 478 includes inner teeth that engage the teeth 465 of the rod member 464 such that the ratchet member 478 can be moved along the rod member 464 as the tension member 429 is rotated. For example, as the tension member 429 is rotated to adjust the tension on the tether, the ratchet member 479 will move with the tension member 429 and the ratchet member 478 will slide relative to the ratchet member 479 until the tension on the tether exceeds a set value, at which point the tensioner 480 will act like a slip clutch, preventing further tensioning. The tension limit can be a preset value of the device or can be set according to the particular procedure and/or patient.

Figure 36:
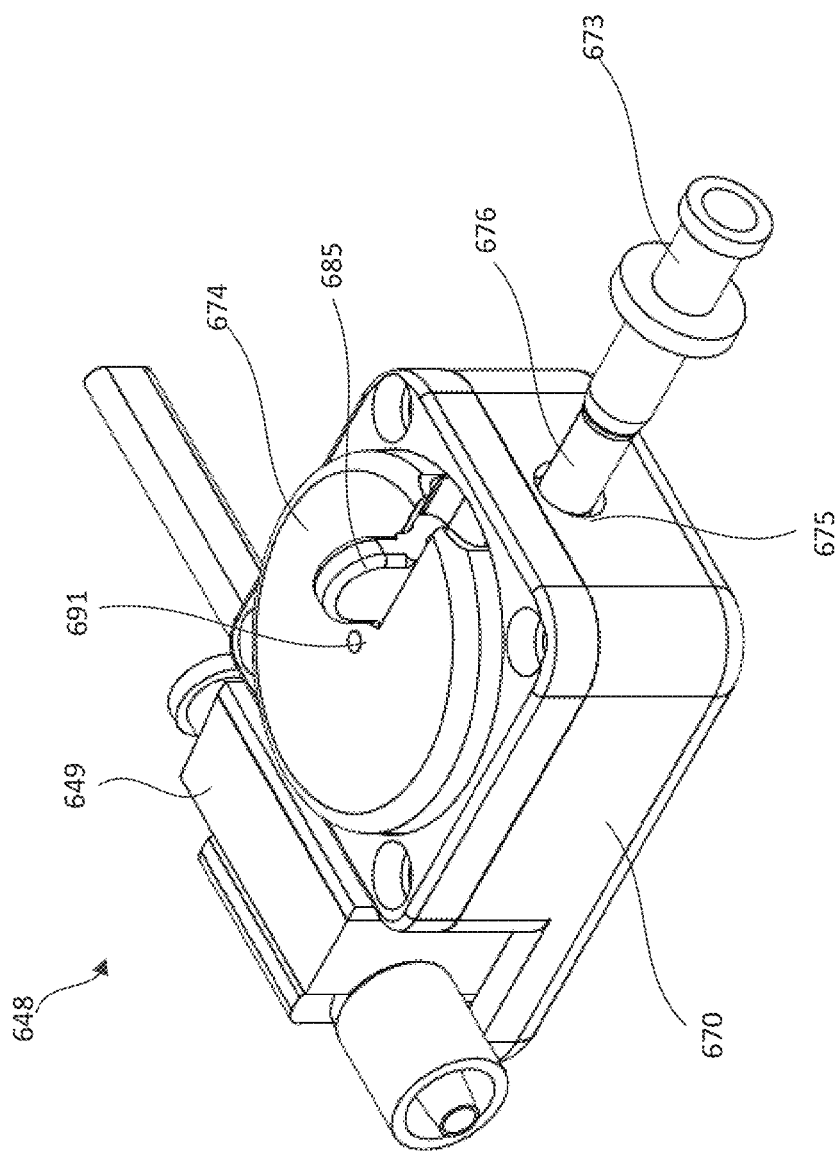
FIG. 36 is a perspective view of a force sensor device according to an embodiment.
Figure 37:
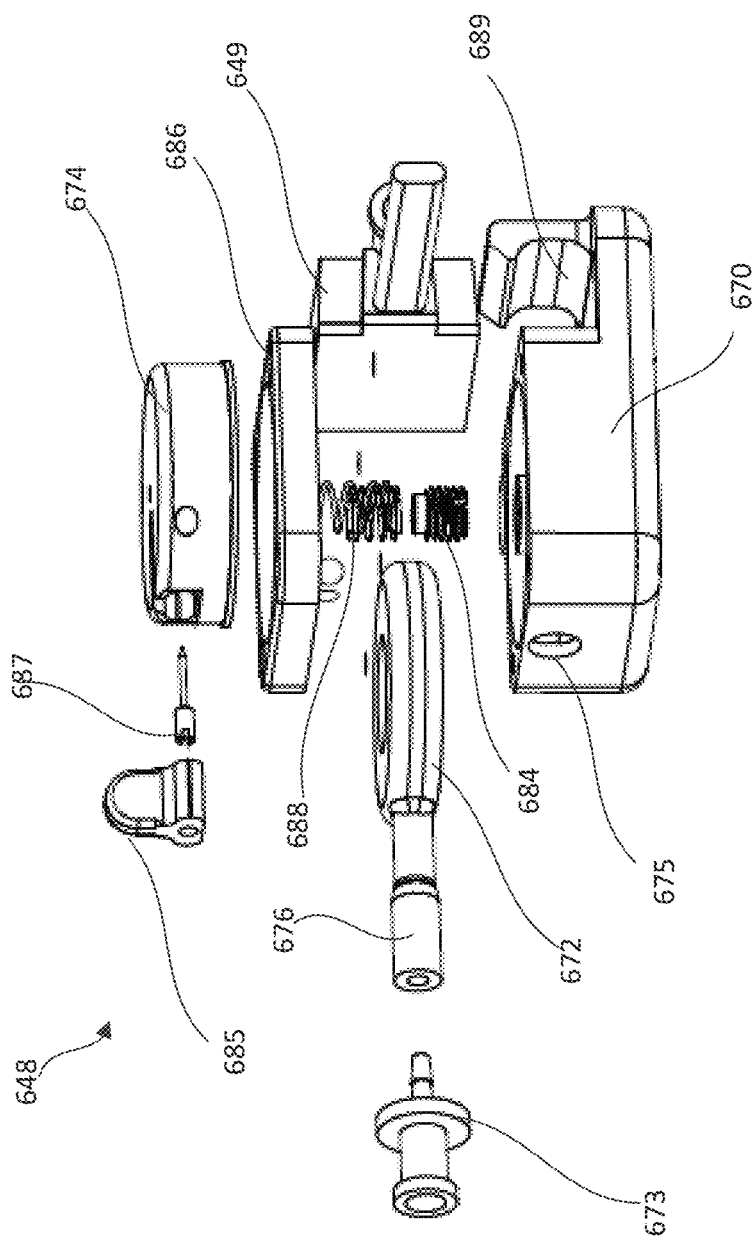
FIG. 37 is an exploded perspective view of the force sensor device of FIG. 36.
Figure 38:
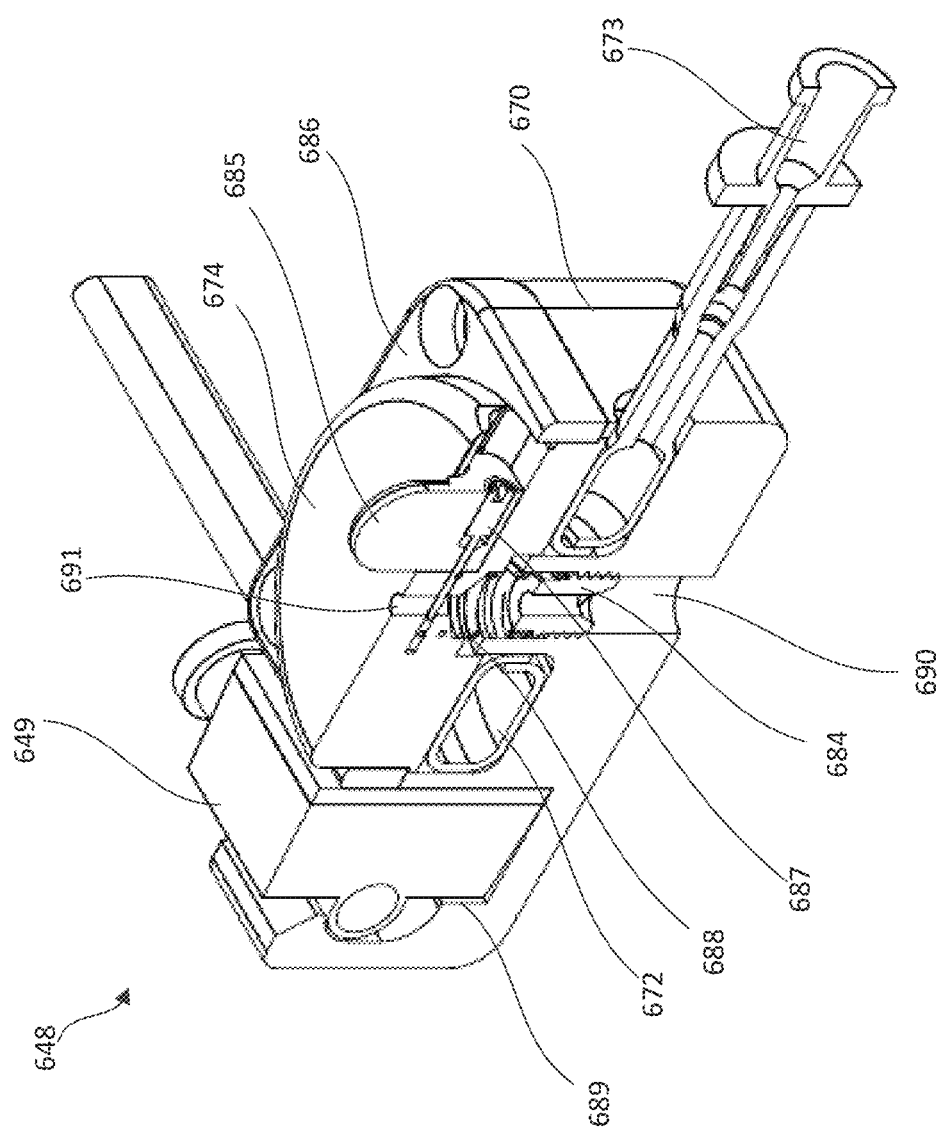
FIG. 38 is a cross-sectional perspective view of the force sensor device of FIG. 36.

FIGS. 36 and 37 illustrate an alternative embodiment of a force sensor device 648 that can be included on a positioning device described herein. The force sensor device 648 is similar to the force sensor device 448 and can function in the same or similar manner as the force sensor device 448. The force sensor device 648 includes a sensor housing 670, a fluid chamber 672 and a load washer 674. The fluid chamber 672 defines an interior region that can contain a fluid and that is in fluid communication with a conduit 676. The fluid chamber 672 is received within the sensor housing 670 and the conduit 676 extends out of the sensor housing 670 through an opening 675 defined by the sensor housing 670. The load washer 674 is disposed over the fluid chamber 672 and is coupled to the sensor housing 670 with a retainer 686 such that the load washer 674 can move or float relative to the sensor housing 670. For example, the load washer includes a perimeter flange (not shown) on which the retainer 686 rests on top of the sensor housing 670. This allows for the fluid chamber 672 to reduce and expand in size within the interior region defined collectively by the sensor housing 670 and the load washer 674. A spring 688 and adjuster screw 684 are disposed within an opening 690 (FIG. 38) defined in the sensor housing 670 and can be used to tune the pressure reading at a fixed load. The opening 690 is also used to couple the force sensor device 648 to a rod member (e.g., 464) of a positioning device (e.g., 642).

In this embodiment, a tether (not shown) extending through the positioning device to which the force sensor device 648 is coupled, extends through the rod member of the positioning device, through the adjuster screw 684 and spring 688, through load washer 674 and out a proximal opening 691 defined in the load washer 674 at a proximal end of the force sensor device 648. In this embodiment, a pinning mechanism incorporated into the force sensor device 648 can be used to pierce the tether and secure the tether to the force sensor device 648. The pinning mechanism includes a pin holder 685 coupled to a pin 687. The pin holder 685 can be manually moved inward to actuate or move the pin 687 inwardly into the opening 691 (see, e.g., FIG. 38) to pierce a tether extending therethrough.

A fluid port connector 673 is coupled to the conduit 676. The fluid port connector 673 can be for example, a Luer connector. The fluid port connector 673 can be coupled to a pressure transducer 649 via a conduit (not shown) which is disposed within a holder portion 689 defined in the sensor housing 670. The pressure transducer 649 being incorporated within the force sensor device 648 can compensate for tool height changes during a procedure that could change the pressure reading. The pressure transducer 649 can in turn be coupled to a device that can be used to display pressure readings received from the pressure transducer 649.

In this embodiment, during use, when the tether is pierced by the pin 687, the load is transferred to the load washer 674, which in turn exerts a compressive force on the fluid chamber 672 causing the pressure of the fluid in the interior region of the fluid chamber 672 to be increased. This increased pressure can be communicated through the fluid from the fluid chamber 672 to and through the conduit 676 and to the pressure transducer 649 via a conduit (not shown) connecting the conduit 676 to the pressure transducer 649 via the connector 673. The force sensor device 648 can be used to measure the load on a tether extending through the positioning device to which the force sensor device 648 is coupled.

For each of the embodiments of a positioning device described herein (242, 342, 442), in some cases, after deployment, the tether may be left having excess length, i.e. not trimmed, in order to facilitate later capture if necessary. If it is determined that the length of the tether is not suitable for some reason, e.g., regurgitation is seen post-procedure and the tether is too slack or the tension is too high and the apical tissue is invaginating or changing the shape of the heart in an unwanted manner, the positioning device can be used to capture the excess untrimmed tail of the tether, thread the tether through the positioning device, re-engage the epicardial anchor device, unlocking the pin assembly of anchor device and allowing for the tether length adjustment. The tether may then be adjusted length-wise, either shorter or longer, and the tether is then re-tested for tensioning force, re-pinned and locked into place with the epicardial anchor device.

In some cases, tether tightening or shortening may be, for example, in the range from about 1 mm-10 mm, or about 1 mm-8 mm, or about 1 mm-5 mm, or about 2 mm-8 mm, or about 2 mm-5 mm in length, and all ranges inclusive. Tether loosening or lengthening is contemplated as ranging from about 1 mm-10 mm, or about 1 mm-8 mm, or about 1 mm-5 mm, or about 2 mm-8 mm, or about 2 mm-5 mm in length and all ranges inclusive.

It is contemplated that the time range for which post-deployment adjustments to the tether length or position can be, for example, from about 0.5 hours-48 hours, or from about 24 hours-72 hours, or from about 1 day-7 days, or from about 1 day-15 days, or from about 1 day-30 days, post-implantation.

In an alternative embodiment of a positioning device, a force sensor device can be included that includes a mechanical indicator. For example, a spring device may be connected to a mechanical tension meter to show load range. A load of 1-2 lbs. or 1-4 lbs. are examples of a typical target load.

Although not shown, an alternative to the vice type of tether securing device described herein (e.g., 247, 347), a pinning device that can be used. For example, such a device can include a portion through which the tether can be threaded, and a pin member can be operatively coupled thereto and actuated to pierce through the tether to hold the tether in position. Such a device can be incorporated into a positioning device and be operatively coupled to an actuation mechanism. In some embodiments, such a pinning mechanism can be manually actuated.

Figure 33:
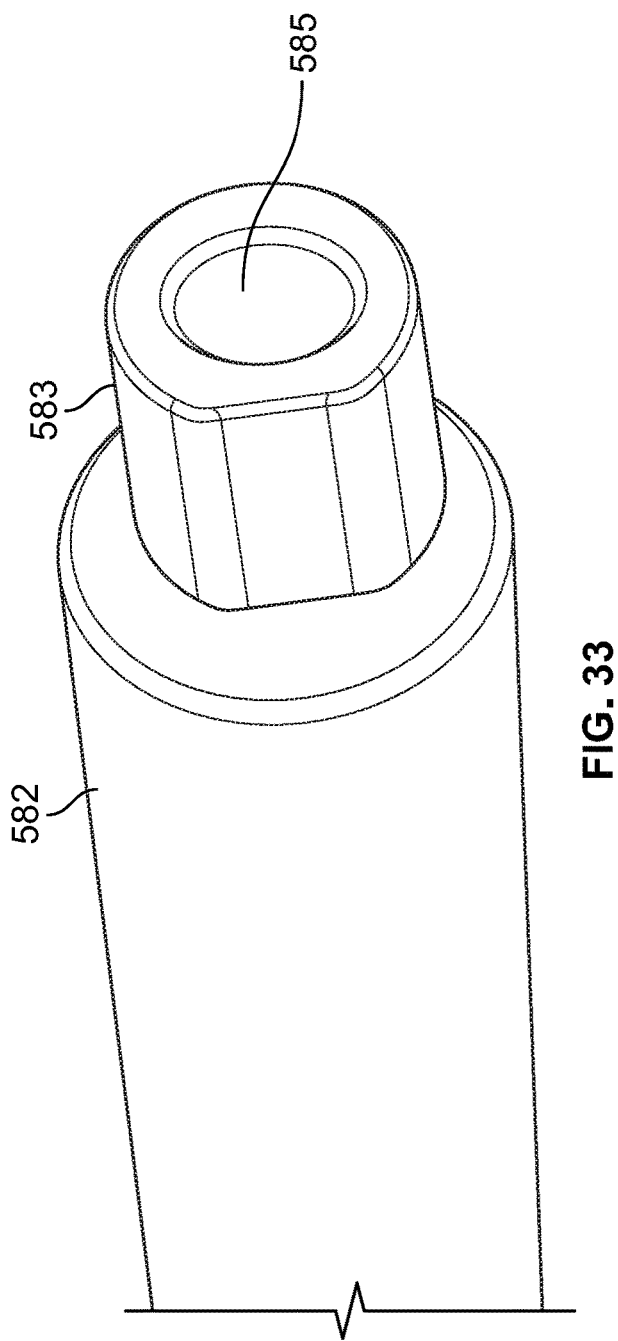
FIG. 33 is a perspective view of an end portion of the tether release tool of FIG. 32.

FIGS. 32-35 illustrate an alternate embodiment of a tether release tool that can be used for capturing a tether, and engaging/re-engaging an epicardial pad after it has been deployed. As shown, for example, in FIGS. 32 and 33, the tether release tool 580 includes a handle 581 coupled to an elongate positioning rod 582. The positioning rod 582 includes a shaped anchor engagement tip 583 and defines a tether capture/recapture access port 584. As shown in FIG. 33, the anchor engagement tip 583 is shaped to be received in a corresponding mating opening 510 of an epicardial anchor device 500 (see, FIGS. 34 and 35), which can be configured the same and function the same as the epicardial anchor device 200 described above. The engagement tip 583 defines an opening 585 that is in fluid communication with the access port 584.

After the epicardial anchor device 500 has been deployed and the tether 528 has been pinned to the anchor device 500, the tether release tool 580 can be used to release the tether to allow the practitioner to make adjustments to the tension on the tether 528 and/or to the position of the anchor device 500. As shown in FIGS. 34 and 35, a portion of the tether 528 extending from the anchor device 528 is inserted through the distal opening 585 and out through the access port 584. The engagement tip 583 can be inserted into the mating opening 510 of the anchor device 500. The tether release tool 580 can be rotated to unlock the locking assembly of the anchor device 500 to release the tether 528 from the anchor device 500. With the tether 528 released, the tension on the tether can be adjusted and/or the position of the anchor device 500 on the heart can be adjusted and then the tether release tool 580 can be used to re-pin the tether 528 to the anchor device. For example, the engagement tip 583 can be inserted into the mating opening 510 of the anchor device 500 and rotated the opposite direction to re-actuate the locking pin assembly of the anchor device 500 and pin the tether 528 to the anchor device 500.

In some embodiments, there is a tether-bundle that attaches to the extended points (two or three or four) of the stent and which converge to a central nexus point to which the adjustable tether is attached and leads to the apical tissue anchor location within the heart. In some embodiments, the tether extends downward through the left ventricle, exiting the left ventricle at the apex of the heart to be fastened on the epicardial surface outside of the heart. Similar anchoring is contemplated herein as it regards the tricuspid, or other valve structure requiring a prosthetic.

As described herein, during deployment of a prosthetic heart valve, the operator is able to adjust or customize the tethers to the correct length for a particular patient's anatomy. The tethers also allow the operator to tighten the cuff onto the tissue around the valvular annulus by pulling the tethers, which creates a leak-free seal. In some embodiments, the tethers are optionally anchored to other tissue locations depending on the particular application of the prosthetic heart valve. In the case of a mitral valve, or the tricuspid valve, there are optionally one or more tethers anchored to one or both papillary muscles, septum, and/or ventricular wall.

The tethers, in conjunction with the cuff of the valve, provide for a compliant valve which has heretofore not been available. The tethers can be made from surgical-grade materials such as biocompatible polymer suture material. Examples of such material include 2-0 exPFTE (polytetrafluoroethylene) or 2-0 polypropylene. In one embodiment, the tethers are inelastic. It is also contemplated that one or more of the tethers may optionally be elastic to provide an even further degree of compliance of the valve during the cardiac cycle. In some embodiments the tether(s) may be bioresorbable/bioabsorbable and thereby provide temporary fixation until other types of fixation take hold such a biological fibrous adhesion between the tissues and prosthesis and/or radial compression from a reduction in the degree of heart chamber dilation.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described. For example, although not necessarily described for each embodiment, the various positioning devices (242, 342, 442) can include any features and or functions described herein for the various embodiments.

What is claimed is:

1. An apparatus, comprising:
a handle assembly coupled to an elongate member;
a docking member coupled to a distal end of the elongate member, the docking member including a plurality of arms configured to be releasably coupled to an epicardial anchor device configured to secure a tether extending from a prosthetic heart valve implanted within a heart at a location on an exterior of a ventricular wall of the heart; and
a force sensor device coupled to the handle assembly, the force sensor device configured to measure a force exerted on the force sensor device, the force associated with a tension of the tether extending through the elongate member and handle assembly, wherein the force sensor device includes a sensor housing, a fluid chamber disposed within the sensor housing and a load washer coupled to the sensor housing such that the fluid chamber is disposed between the sensor housing and the load washer, the fluid chamber containing a volume of fluid, the volume of fluid being displaced when the force is exerted on the force sensor device.

2. The apparatus of claim 1, further comprising:
a tether securing device coupled to the handle assembly proximal to the force sensor device, the tether securing device configured to secure the tether extending through the elongate member and handle assembly at a fixed position relative to the handle assembly.

3. The apparatus of claim 1, further comprising:
a tether securing device coupled to the handle assembly proximal to the force sensor device, the tether securing device configured to secure the tether extending through the elongate member and handle assembly at a fixed position relative to the handle assembly,
the tether securing device configured to contact the force sensor device and exert the force on the force sensor device as the tether is pulled proximally to a desired tension.

4. The apparatus of claim 1, further comprising:
a rod member coupled to the handle assembly; and
a tension member coupled to the rod member, the tension member configured to be moved distally relative to the rod member to adjust the tension on the tether extending through the elongate member and handle assembly.

5. The apparatus of claim 1, further comprising:
a rod member coupled to the handle assembly; and
a tension member coupled to the rod member, the rod member configured to be moved proximally when the tension member is rotated to adjust the tension on the tether extending through the elongate member and handle assembly.

6. The apparatus of claim 1, further comprising:
a rod member coupled to the handle assembly, the rod member having an indicator disposed at a distal end of the rod member,
the handle assembly including a transparent segment with indications, the indicator disposed at the distal end of the rod member being viewable through the transparent segment, the tether extending through the apparatus having a marker disposed thereon,
a location of the indicator relative to the indications on the transparent segment corresponding to a distance between a surface of the epicardial anchor device contacting the heart and an annulus of the heart when the marker on the tether is disposed proximal to a proximal end of the apparatus.

7. The apparatus of claim 1, wherein the handle assembly further comprises a dial, and the docking member further comprises a distal tip operably coupled to the distal end of the elongate member and configured to be received within the anchor device.

8. A method, comprising:
inserting a tether through an epicardial anchor device, the tether extending from a prosthetic heart valve implanted within the heart, the tether extending outside of the heart,
inserting the tether through a positioning device such that a proximal end of the tether extends outside a proximal end of the positioning device;
coupling the epicardial anchor device to a docking member disposed at a distal end of the positioning device;
pulling the tether proximally until a desired tension on the tether is achieved;
positioning the epicardial anchor device at a desired location on an outside wall of the heart;

after the positioning, securing the tether to the epicardial anchor device; and releasing the epicardial anchor device from the docking member.

9. The method of claim 8, further comprising:

prior to securing the tether to the epicardial anchor device, securing a proximal end portion of the tether to a tether securing device disposed at the proximal end of the positioning device;

increasing the tension on the tether by moving the epicardial anchor device distally while holding the tether securing device in a fixed position; and releasing the tether from the tether securing device.

10. The method of claim 9, wherein the moving the epicardial anchor device distally includes moving distally a tension member coupled to a rod member of the positioning device, the moving of the tension member configured to move distally a handle assembly, elongate member and the docking member of the positioning device.

11. The method of claim 8, further comprising:

prior to the securing the tether to the epicardial anchor device, securing a proximal end portion of the tether to a tether securing device disposed at the proximal end of the positioning device;

increasing the tension on the tether by moving the tether securing device with the tether secured thereto proximally relative to the epicardial anchor device; and releasing the tether from the tether securing device.

12. The method of claim 11, wherein the positioning device includes a tension member coupled to a rod member, the tether securing device coupled to the rod member, the increasing the tension on the tether includes rotating the tension member such that the rod member and tether securing device are both moved proximally relative to the epicardial anchor device.

13. The method of claim 8, wherein the positioning device includes a force sensor device, the method further comprising:

prior to the securing the tether to the epicardial anchor device, measuring a force exerted on the force sensor device, the force associated with a tension of the tether extending through the positioning device.

14. The method of claim 13, wherein the force sensor device includes a sensor housing, a fluid chamber disposed within the sensor housing and a load washer coupled to the sensor housing such that the fluid chamber is disposed between the sensor housing and the load washer, the measuring the force includes measuring a displacement of a volume of fluid disposed within the fluid chamber when a force is exerted on the load washer.

15. The method of claim 13, wherein the force sensor device includes a sensor housing and a load cell disposed within an interior of the sensor housing, the measuring the force includes measuring a deflection on the load cell caused by a force being exerted on the load cell.

16. An apparatus, comprising:

a handle assembly coupled to an elongate member;

a docking member coupled to a distal end of the elongate member, the docking member including a plurality of arms configured to be releasably coupled to an epicardial anchor device configured to secure a tether extending from a prosthetic heart valve implanted with a heart at a location on an exterior of a ventricular wall of the heart; and a tether securing device coupled to the handle assembly proximal to the handle assembly, the tether securing device configured to secure the tether extending through the elongate member and handle assembly at a fixed position relative to the handle assembly.

17. The apparatus of claim 16, further comprising:

a rod member coupled to the handle assembly; and a tension member coupled to the rod member, the tension member configured to be moved distally relative to the rod member to adjust the tension on a tether extending through the elongate member and handle assembly when the tether is secured to the tether securing device.

18. The apparatus of claim 16, further comprising:

a rod member coupled to the handle assembly; and a tension member coupled to the rod member, the rod member configured to be moved proximally when the tension member is rotated to adjust the tension on a tether extending through the elongate member and handle assembly.

19. The apparatus of claim 16, further comprising:

a rod member coupled to the handle assembly, the rod member having an indicator disposed at a distal end of the rod member, the handle assembly including a transparent segment with indications, the indicator disposed at the distal end of the rod member being viewable through the transparent segment, a tether extending through the elongate member and handle assembly having a marker disposed thereon, a location of the indicator relative to the indications on the transparent segment corresponding to a distance between a surface of the epicardial anchor device contacting the heart and an annulus of the heart when the marker on the tether is disposed proximal to a proximal end of the apparatus.

20. The apparatus of claim 16, wherein the handle assembly further comprises a dial, and the docking member further comprises a distal tip operably coupled to the distal end of the elongate member and configured to be received within the anchor device.

* * * * *